US007897078B2

(12) United States Patent
Petersen et al.

(10) Patent No.: US 7,897,078 B2
(45) Date of Patent: Mar. 1, 2011

(54) METHODS OF MANUFACTURING A STRETCHED MECHANICAL FASTENING WEB LAMINATE

(75) Inventors: Johann F. Petersen, Grevenbroich (DE); Ralf G. Oertel, Neuss (DE); Ronald W. Ausen, St. Paul, MN (US); Janet A. Venne, Roseville, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 821 days.

(21) Appl. No.: 10/796,702

(22) Filed: Mar. 9, 2004

(65) Prior Publication Data

US 2005/0202205 A1 Sep. 15, 2005

(51) Int. Cl.

| | |
|---|---|
| ***D01D 5/20*** | (2006.01) |
| ***B32B 1/00*** | (2006.01) |
| ***B29C 55/00*** | (2006.01) |
| *A44B 18/00* | (2006.01) |

(52) U.S. Cl. ........................ 264/167; 264/148; 264/151; 264/171.13; 264/173.1; 264/210.1; 264/210.7; 264/257; 264/259; 264/288.4; 264/288.8; 264/290.2; 156/229; 156/244.11; 156/244.27; 24/451; 428/100

(58) Field of Classification Search ........................ None
See application file for complete search history.

(56) References Cited

U.S. PATENT DOCUMENTS 3,169,899 A * 2/1965 Steuber ........................ 428/198
3,276,944 A 10/1966 Levy (Continued)

FOREIGN PATENT DOCUMENTS

EP 0 894 448 B1 5/2001

(Continued)

*Primary Examiner*—Jeffrey Wollschlager
(74) *Attorney, Agent, or Firm*—Kathleen B. Gross; William J. Bond

(57) ABSTRACT

The present invention relates to a method of manufacturing a stretched mechanical fastening web laminate (1) comprising a thermoplastic web layer (13) having two major surfaces, one of the major surfaces bearing a multitude of male fastening elements (14) suitable for engagement with a corresponding female fastening material, and on its other major surface a fibrous web layer (11), said method comprising the steps of (i) providing the fibrous web layer (11) having an initial basis weight, (ii) passing the fibrous web layer (11) through a nip formed by two rolls (101), (103), one of them having cavities (120) that are the negatives of a plurality of male fastening elements (14), introducing a molten thermoplastic resin into the cavities (120) in excess of an amount that would fill the cavities (120) which excess forms the thermoplastic web layer (13), allowing the resin to at least partially solidify and stripping of a precursor web laminate (10) thus formed comprising the fibrous web layer (11) and the thermoplastic web layer (13) bearing a plurality of male fastening elements (14), from the cylindrical roll (103) having cavities (120) whereby the thermoplastic web layer (13) has an initial thickness and an initial hook density, and (iii) stretching the precursor web laminate (10) monoaxially or biaxially thereby decreasing the basis weight of the fibrous web layer (11) and the thickness of the thermoplastic web layer (13) from their respective initial values to provide a stretched mechanical fastening laminate (1) having a basis weight of less than 100 $g \cdot m^{-2}$.

24 Claims, 6 Drawing Sheets

U.S. PATENT DOCUMENTS 3,324,218 A * 6/1967 Gebler et al. ............ 526/348.1
3,338,992 A 8/1967 Kinney
3,341,394 A 9/1967 Kinney
3,502,538 A 3/1970 Petersen
3,502,763 A 3/1970 Hartmann
3,542,615 A 11/1970 Dobo et al.
3,692,618 A 9/1972 Dorschner et al.
3,903,234 A 9/1975 Ikeda et al.
3,995,007 A 11/1976 Nakamura et al.
4,056,593 A * 11/1977 de Navas Albareda ...... 264/145
4,187,586 A * 2/1980 Semjonow ................ 19/161.1
4,330,499 A 5/1982 von und zu Aufsess et al.
4,335,069 A 6/1982 Levy
4,336,804 A 6/1982 Roeder
4,340,563 A 7/1982 Appel et al.
4,475,913 A 10/1984 Hlaban
4,595,738 A 6/1986 Hufnagel et al.
4,675,582 A 6/1987 Hommes et al.
4,775,310 A 10/1988 Fischer
4,794,028 A 12/1988 Fischer
4,825,111 A 4/1989 Hommes et al.
4,853,062 A 8/1989 Gartland
4,872,243 A 10/1989 Fischer
4,894,060 A 1/1990 Nestegard
4,959,245 A 9/1990 Dobson et al.
5,036,262 A 7/1991 Schonback
5,051,225 A 9/1991 Hommes et al.
5,072,493 A 12/1991 Hommes et al.
5,260,015 A * 11/1993 Kennedy et al. ............ 264/167
5,429,854 A 7/1995 Currie et al.
5,507,735 A 4/1996 Van Iten et al.
5,534,215 A * 7/1996 Song et al. .................. 264/345
5,611,790 A 3/1997 Osborn, III et al.
5,616,155 A * 4/1997 Kronzer ....................... 51/295
5,669,900 A 9/1997 Bullwinkel et al.
5,690,875 A 11/1997 Sakakibara et al.
5,744,080 A * 4/1998 Kennedy et al. ............ 264/167
5,755,015 A 5/1998 Akeno et al.
5,778,457 A 7/1998 Conway
5,785,784 A 7/1998 Chesley et al.
5,875,527 A 3/1999 Lacey et al.
5,900,350 A 5/1999 Provost et al.
5,971,738 A 10/1999 Jens et al.
5,985,407 A 11/1999 Murasaki
6,039,712 A 3/2000 Fogarty et al.
6,054,091 A * 4/2000 Miller et al. ................ 264/442
6,174,476 B1 * 1/2001 Kennedy et al. ............ 264/167
6,190,594 B1 2/2001 Gorman et al.
6,329,016 B1 * 12/2001 Shepard et al. ............. 427/173
6,342,285 B1 * 1/2002 Shepard et al. ............... 428/88
6,443,932 B1 9/2002 Maggiulli
6,484,371 B1 * 11/2002 Romanko et al. ............. 24/306
6,582,642 B1 6/2003 Buzzell et al.
6,598,276 B2 * 7/2003 Shepard et al. ................ 26/51
6,660,202 B2 * 12/2003 Shepard et al. ............. 264/167
6,668,435 B2 * 12/2003 Wood et al. ................... 28/162
6,814,912 B2 * 11/2004 Ausen et al. ................ 264/145
6,942,896 B1 * 9/2005 Martin ....................... 427/336
6,955,847 B1 * 10/2005 Itou et al. ................... 428/174
7,052,636 B2 * 5/2006 Ausen et al. ................ 264/145
7,223,314 B2 * 5/2007 Provost ...................... 156/259
7,303,805 B2 12/2007 Seth et al.
2002/0090418 A1 7/2002 Prevost et al.

FOREIGN PATENT DOCUMENTS

| | | |
|---|---|---|
| JP | 3-021202 | 1/1991 |
| WO | WO 98/53781 | 12/1998 |
| WO | WO 98/53782 | 12/1998 |
| WO | WO 03/059108 | 7/2003 |

* cited by examiner 1
14 13
11
10
14
13
11
105
11
14
103
101
104
100
102

MD tensile strength at break [N/25 mm]
Basis weight [g/m²]
55.0
50.0
45.0
40.0
35.0
30.0
25.0
20.0
15.0
10.0
5.0
0.0
70.0
65.0
60.0
55.0
50.0
45.0
40.0
35.0
30.0
25.0
20.0
15.0
10.0
5.0
0.0
5

METHODS OF MANUFACTURING A STRETCHED MECHANICAL FASTENING WEB LAMINATE

FIELD OF THE INVENTION

The present invention relates to methods of manufacturing a stretched mechanical fastening web laminate and to stretched mechanical fastening web laminates which are obtainable by such method. The present invention also relates to disposable absorbent articles such as diapers, sanitary napkins, pantyliners and incontinence pads comprising a portion of the mechanical fastening web laminate obtained from the corresponding mechanical fastening web laminate, for example, by cutting.

BACKGROUND OF THE INVENTION

U.S. Pat. No. 6,582,642 discloses a method of producing a sheet form fastener product comprising a. lengthwise stretching a sheet of heat-softened synthetic resin to pre-orient the molecular structure of the sheet in a longitudinal direction;

b. with a rotating mold roll, molding from said lengthwise-stretched sheet a running web having a base and a multiplicity of discrete fastener elements integral with the base and protruding from at least one side of the base; and c. thereafter, under conditions in which the web is permanently stretchable, stretching the web widthwise in a manner that permanently stretches the base and increases the widthwise spacing of the fastener elements.

In a specific embodiment illustrated in FIG. 13 of U.S. Pat. No. 6,582,642, it is suggested to feed a precompressed knitted web into a nip comprising said rotating mold roll thereby creating an integrated laminate comprising the knitted web and the web having a base and a multiplicity of discrete fastening elements integral with the base. The precompressed knitted web does not tend to shorten longitudinally upon stretching the laminate widthwise so that the thickness of the knitted web is not decreased to a major extent. Stretching of non-precompressed knitted webs is furthermore difficult to perform.

U.S. Pat. No. 6,484,371 discloses a mechanical fastener comprising a hook web and a loop material applied to a first major surface of such hook web. The hook web comprises a uniaxially oriented polymeric substrate bearing a plurality of hooks disposed on the second major surface of the hook web opposite to the first major surface. The thickness and/or mechanical strength of the mechanical fastener of U.S. Pat. No. 6,484,371 does not always meet all practical requirements of disposable sanitary articles and, in particular, of sanitary napkins.

Disposable articles such as sanitary napkins comprise a liquid pervious top sheet which is attached towards the body of the wearer, and a liquid impervious back sheet facing away from the body of the wearer. The top sheet and the back sheet sandwich an absorbent core designed to absorb body exudates such as blood, menses, urine and excrements which are discharged from the body.

In a sanitary napkin, the back sheet is intended to be placed adjacent to the wearer's undergarments and may comprise adhesive and/or male mechanical fastening means such as hook fastener elements to securely attach the sanitary napkin to the undergarment which mechanically engages with the hook fastener elements. A back sheet comprising mechanical fastening means preferably is thin and flexible so that it does not significantly contribute to the overall thickness of the sanitary napkin and does not result in discomfort when attached to the wearer's body. The back sheet also preferably exhibits a sufficient mechanical strength and, in particular, a sufficient tensile strength and tear resistance so that it can be safely handled during the manufacturing of the sanitary napkin and during its use without rupturing.

It was therefore an object of the present invention to provide a mechanically stable, thin web material which can be advantageously used, for example, as a back sheet in sanitary napkins. It was another object of the present invention to provide a stretched mechanical fastening web having a low overall thickness and basis weight. The person skilled in the art can easily take other objects of the invention from the following detailed description.

SUMMARY OF THE INVENTION

The present invention relates to a first method of manufacturing a stretched mechanical fastening web laminate comprising a thermoplastic web layer having two major surfaces, one of the major surfaces bearing a multitude of male fastening elements suitable for engagement with a corresponding female fastening material, and on its other major surface a fibrous web layer, said method comprising the steps of (i) providing a fibrous web layer having an initial basis weight, (ii) passing the fibrous web layer through a nip formed by two rolls, one of them having cavities that are negatives of a plurality of male fastening elements, introducing a molten thermoplastic resin into the cavities in excess of an amount that would fill the cavities which excess forms the thermoplastic web layer, allowing the resin to at least partially solidify and stripping of a precursor web laminate thus formed comprising the fibrous web layer and the thermoplastic web layer bearing the multitude of male fastening elements from the roll having cavities, wherein the thermoplastic web layer has an initial thickness and an initial density of male fastening elements, and (iii) stretching the precursor web laminate monoaxially or biaxially thereby decreasing the basis weight of the fibrous web layer and the thickness of the thermoplastic web layer from their respective initial values to provide a stretched mechanical fastening laminate having a basis weight of less than 100 g/m$^2$.

The present invention relates to a second method of manufacturing a stretched mechanical fastening web laminate comprising a thermoplastic web layer having two major surfaces, one of the major surfaces bearing a multitude of male fastening elements suitable for engagement with a corresponding female fastening material, and on its other major surface a fibrous web layer, said method comprising the steps of (i) extruding the thermoplastic web layer bearing on one major surface a plurality of elongate spaced ribs in a machine direction with the cross-sectional shape of the ribs essentially corresponding to the cross-sectional shape of the male fastening elements to be formed, wherein the thermoplastic web layer has an initial thickness, (ii) providing the fibrous web layer having an initial basis weight, (iii) extrusion-laminating the fibrous web layer to the major surface of the thermoplastic web layer opposite to the major surface bearing the elongate spaced ribs, thus providing a precursor web laminate, (iv) slitting the ribs in a cross-direction at spaced locations to form discrete portions of the ribs in the cross-direction with a length in the direction of the ribs essentially corresponding to a desired length of the male fastening elements to be formed, and stretching the precursor web laminate monoaxially or biaxially thereby decreasing the basis weight of the fibrous web layer and the thickness of the thermoplastic web layer from their respective initial values to provide a stretched mechanical fastening laminate having a basis weight of less than 100 g/m$^2$.

The present invention also relates to a stretched mechanical fastening web laminate obtainable by the methods according to the present invention, said stretched mechanical fastening web laminate comprising a thermoplastic web layer having two major surfaces, one of the major surfaces hearing a multitude of male fastening elements suitable for engagement with a corresponding female fastening material, and on its other major surface a fibrous web layer, the stretched mechanical fastening laminate having been stretched to provide a basis weight of less than 100 g/m$^2$.

The present invention also relates to a disposable absorbent article comprising a portion of the stretched mechanical fastening web laminate according to the invention.

DETAILED DESCRIPTION OF THE INVENTION

Figure 1A:
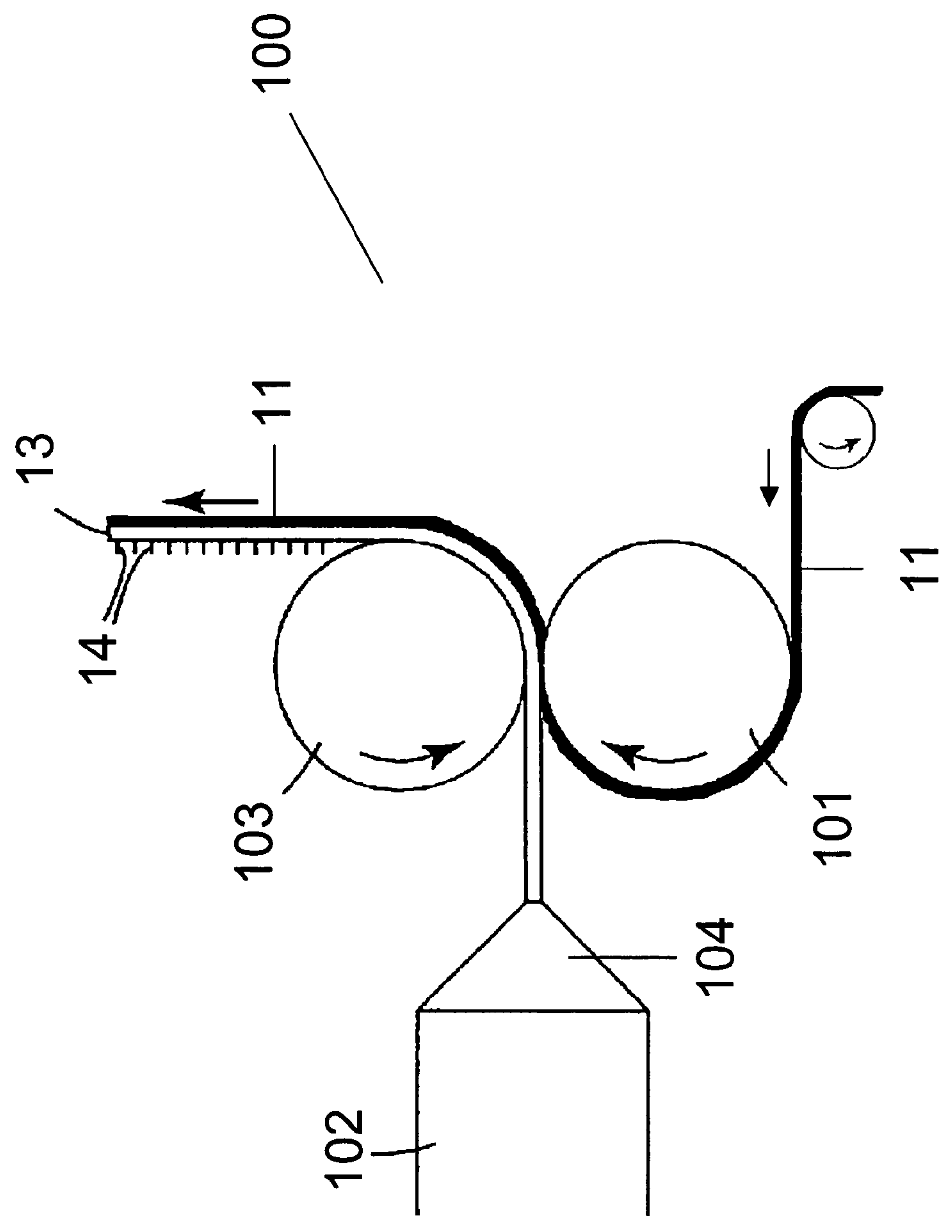
FIG. 1*a* is a schematic diagram of a first embodiment of an apparatus 100 suitable for making a precursor web laminate 10.

The present invention relates to a stretched mechanical fastening web laminate 1 having a basis weight of less than 100 g·m$^{-2}$ which is obtainable by monoaxially or biaxially stretching a precursor web laminate 10 comprising a fibrous web layer 11 and a thermoplastic web layer 13 bearing a multitude of male fastening elements 14 suitable for engagement with a corresponding female fastening material. The stretched mechanical fastening web laminate 1 comprises a stretched fibrous web layer 11 having a basis weight which is decreased with respect to the initial value of the basis weight of the fibrous web layer 11. Likewise, the thickness of the thermoplastic web layer 13 of the stretched mechanical fastening web laminate 1 is less than the thickness of the corresponding thermoplastic web layer 13 of the precursor laminate 10. Surprisingly the male fastening elements 14 are generally not substantially deformed upon stretching and at any rate not to an extent that would render them non-functional with respect to the corresponding female fastening material.

Above and below, the same reference numbers will be used for the corresponding layers and elements (i.e. the fibrous web layer 11, the thermoplastic web layer 13 and the male fastening elements 14) of the precursor web laminate 10 and the stretched mechanical fastening web laminate 1 of the present invention, respectively.

In the first step (i) of the first method according to the present invention, a fibrous web layer 11 having an initial basis weight is provided.

Fibrous web layers 11 which may be used in the present invention include nonwoven materials and mixed fabrics comprising a blend of nonwoven materials with other fibrous materials such as woven or knitted materials. Nonwoven fibrous web layers 11 are preferred. The fibrous web layer 11 preferably has an initial basis weight of between 10-400 g/m$^2$, more preferably of between 20-300 g/m$^2$ and especially preferably of between 30-250 g/m$^2$.

Nonwoven fibrous web layers 11 which are highly preferred, are preferably formed from filaments. The term "filament" as used herein defines a member having a high ratio of length to diameter or width, and thus may be a fiber, a thread, a strand, a yarn or any other member or combination of these members.

The nonwoven fibrous web layer 11 may comprise filaments having similar or different titers. Preferably, the filaments are selected so that the filaments exhibit an average titer of from 0.5 to 10 dtex and more preferably from 0.5 to 5 dtex.

The length of the filaments varies depending on the method used for forming the web. For spunbond nonwoven web endless filaments are used whereas staple fibers in bonded carded webs preferably have a length of up to 10 cm and preferably of between 1-8 cm.

The nonwoven fibrous web layer 11 may further comprise a mixture of filaments comprising different materials.

Suitable processes for making fibrous web layers 11 of nonwoven materials include but are not limited to airlaying, spunbonding, spunlacing, hydroentanglement, bonding of melt blown webs and bonding of carded webs.

Spunbond nonwoven fibrous web layers 11 are made, for example, by extruding a molten thermoplastic as filaments from a series of fine die orifices in a spinneret. The diameter of the extruded filaments is rapidly reduced under tension by, for example, non-eductive or eductive fluid-drawing or other known spunbond mechanisms, such as described in U.S. Pat. Nos. 4,340,563, 3,692,618, 3,338,992, 3,341,394, 3,276,944, 3,502,538, 3,502,763 and 3,542,615. The spunbond nonwoven fibrous web layer 11 is preferably bonded (point or continuous bonding).

The nonwoven fibrous web layer 11 may also be made from bonded carded webs. Carded webs are made from separated staple fibers, which fibers are sent through a combing or carding unit which separates and aligns the staple fibers in the machine direction so as to form a generally machine direction-oriented fibrous nonwoven web. However, randomizers can be used to reduce this machine direction orientation. Once the carded web has been formed, it is then bonded by one or more of several bonding methods to give it suitable tensile properties. One bonding method is powder bonding wherein a powdered adhesive is distributed through the web and then activated, usually by heating the web and adhesive with hot air. Another bonding method is pattern bonding wherein heated calender rolls or ultrasonic bonding equipment are used to bond the fibers together, usually in a localized bond pattern though the web can be bonded across its entire surface if so desired. Generally, the more the fibers of a web are bonded together, the greater the tensile properties of the nonwoven web layer 11.

Airlaying is another process by which nonwoven fibrous web layers 11 useful in the present invention can be made. In the airlaying process, bundles of small fibers usually having lengths ranging between about 6 to about 19 millimeters are separated and entrained in an air supply and then deposited onto a forming screen, often with the assistance of a vacuum supply. The randomly deposited fibers are then bonded to one another using, for example, hot air or a spray adhesive.

Meltblown nonwoven fibrous web layers 11 may be formed by extrusion of thermoplastic polymers from multiple die orifices, which polymer melt streams are immediately attenuated by hot high velocity air or steam along two faces of the die immediately at the location where the polymer exits from the die orifices. The resulting fibers are entangled into a coherent web layer in the resulting turbulent airstream prior to collection on a collecting surface. Generally, to provide sufficient integrity and strength, meltblown fibrous web layers 11 must be further bonded such as by through air bonding, heat or ultrasonic bonding as described above.

The fibrous web layer 11 may comprise in addition to the fibrous layer a supporting base layer to which the fibrous layer is secured. The base layer may be formed, for example, from a thermoplastic resin selected, for example, from a group of polymers comprising polyesters, polyamides, poly(acrylonitrile-butadiene-styrenes) and polyolefins. The base layer tends to increase the mechanical strength and handleability of the fibrous web layer 11. If a base layer is present, the fibrous web layer 11 is fed into the nip formed by rolls 101 and 103 so that the base layer is facing the roll 101.

The fibrous web layer 11 may be provided as a prefabricated material and fed in step (ii) of the method of the present invention into the nip formed by two cylindrical rollers 101, 103 one of them (which is referred to above and below as tool roll 103) having cavities 120 that are the negatives of a plurality of male fastening elements 14. Alternatively, it is also possible to prepare the fibrous web layer 11 in line and channel it directly into said nip. It was found that the stretchability of the precursor web laminate 10 is improved and the formation of inhomogenities in the stretched mechanical fastening web laminate 1 is decreased if the fibrous web layer 11 is formed in line and laminated, directly upon forming, to the thermoplastic web layer 13 with essentially immediate subsequent stretching. If the fibrous web layer 11 is formed off-line and stored prior to the formation of the precursor web laminate 10, the storage time of the fibrous web layers 11 preferably is less than 10 weeks, more preferably less than 5 weeks and especially preferably not more than 3 weeks.

In the second step (ii) of the first method of the present invention a molten thermoplastic resin which may be supplied, for example, from an extruder 102 through a die 104 or by cast molding, is injected into the nip in an excess of an amount that would fill the cavities so that a thermoplastic web layer 13 bearing male fastening elements 14, is formed.

Substantially any thermoplastic material suitable for film production can be used to produce the thermoplastic web layer 13 and the male fastening elements 14. Preferred thermoplastic resins include polyesters such as poly(ethylene terephthalate), polyamides such as nylon, poly(styrene-acrylonitrile), poly(acrylonitrile-butadiene-styrene), polyolefins such as polyethylene or polypropylene, plasticized polyvinylchlorides and any mixture of such materials.

It is also possible to use different thermoplastic materials for the formation of the thermoplastic web layer 13 and the male fastening elements. This can he obtained, for example, by using in the apparatus of FIG. 1*a* with two different extruders 102, 102' and two different dies 104, 104' (102' and 104' not shown in FIG. 1*a*) which supply two layers of molten thermoplastic materials being superpositioned with respect to each other, into the nip between rolls 101 and 103 so that the male fastening elements 14 are essentially formed by one of the thermoplastic materials and the thermoplastic web layer by the other thermoplastic material.

The thermoplastic material used for the formation of the male fastening elements 14 may be selected to impart specific properties to them such as, for example, a high coefficient of friction and thus anti-skid properties, tackiness or a higher elasticity or stretchability (in comparison to the corresponding elasticity and stretchability of the resin used for the formation of the thermoplastic resin layer 13). Suitable thermoplastic materials which tend to impart anti-skid properties to the male fastening elements 14 preferably have a Vicat softening point of less than 80° C. and more preferably of between 35-75° C. The Vicat softening point is evaluated according to ISO 306:1994(E) using a force of 10 N by which the steel rod with its indenting tip is pressed onto the polymer example, and a temperature increase rate of 120° C./h. Suitable thermoplastic polymers imparting anti-skid properties to the male fastening elements include very low density polyethylenes (VLDPEs) having a density of 0,900 g/cm$^3$ or less. These materials are commercially available, for example, from Dow Plastics as AFFINITY series polyolefin plastomer materials or from Dupont Dow Elastomers as ENGAGE series polyolefin plastomers. Another class of suitable materials imparts anti-skid properties to the male fastening elements 14, includes E/VA copolymers comprising ethylene as a first comonomer and vinyl acetate as a second comonomer, and ethylene/alkyl(meth)acrylate copolymers. The E/VA and E/A(M)A copolymers, respectively, which are useful in the present invention preferably have a melt-flow index of 0.5-20 and more preferably of 2-10.

It is preferred that the thermoplastic materials providing anti-skid properties are used for the formation of the male fastening elements 14 while a different thermoplastic material providing more mechanical strength is used for the formation of the thermoplastic web layer 13. It is, however, also possible that thermoplastic materials providing anti-skid properties are used for the formation of both the male fastening elements 14 and the thermoplastic web layer 13.

The tool rolls 103 which may be used in the method of the present invention include a plurality of cavities 120 in their outer surface that, when supplied, with the molten thermoplastic resin, can form male fastening elements 14 or their precursors on the surface of the thermoplastic layer 13.

Suitable tool rolls 103 and their method of manufacturing are disclosed, for example, in U.S. Pat. No. 6,190,594. The tool rolls 103 of U.S. Pat. No. '594 are constructed of a cylindrical base roll and are wrapped with one or more continuous wires in a helical pattern. The wires are used to form a structured surface on the tool roll 103 that is the negative of the male fastening elements 14 to be formed on the thermoplastic web layer 13. FIG. 1*b* shows a schematic exploded view of the manufacturing process of a preferred embodiment of a tool roll 103. The wire 123 comprising voids forming upon winding the cavities 120, is wound in a helical fashion around the cylindrical base roll 125. In the specific embodiment of FIG. 1*b* the wire 123 comprises a first wire comprising the voids and a second continuous spacer wire which are wound in an alternating fashion around the cylindrical base roll 125. FIG. 1*c* shows a schematic cross-sectional view of the tool roll 103 of FIG. 1*b*.

In the specific embodiment of FIG. 1*c* a coating or plating 121 is attached to the exposed surface of the wire 123 to impart surface properties such as, for example, increased wear resistance, controlled release characteristics, controlled surface roughness, bonding between adjacent wire windings etc. to the wire 123. The coating 121, if present, is preferably selected so that the adhesion of the thermoplastic resin to the wires 123 and/or the cylindrical base roll 125 is less than the cohesion of such thermoplastic resin at the time of the removal of the precursor web laminate 10 from the tool roll 103.

The cavities 120 shown in FIG. 1*b* and 1*c* have an essentially rectangular cross-section but other cross-sectional shapes such as, for example, round, elliptical, prismatic, pyramidal, cone-shaped cross-sections, curved cross-sections, for example, in the form of a hook or a double-hook, tub-shaped cross-sections which exhibit a wider cross-sectional extension in the middle of the cavity 120 as compared to the cross-sectional extension at its top, i.e. at the opening, and/or its bottom. The cavities 120 shown in FIGS. 1*b,c* are arranged with respect to the cylindrical base roll 125 so that the longitudinal axis extending from the top to the bottom of the cavities 120, is essentially perpendicular to the surface of the cylindrical base roll. It is, however, also possible that the longitudinal axis of the cavities 120 is arranged in an oblique fashion with respect to the cylindrical base roll 125 so that such longitudinal axis forms an angle with the direction normal to the surface of the cylindrical base roll 125.

The specific embodiment of the tool roll 103 described above is given by way of example only and the person skilled in the art can modify the construction of the wires so that any shape of cavities resulting in suitable male fastening elements 14 can be used. The passage from col. 4, line 35 to col. 10, line 40 of U.S. Pat. No. 6,190,594 describing other specifically preferred embodiments, is included herewith by reference. FIGS. 1*b* and 1*c* were taken from U.S. Pat. No. '594.

The tool rolls 103 described above are to explain the invention only without limiting it.

Other suitable tool rolls 103 and methods for their manufacturing are described, for example, in U.S. Pat. Nos. 4,775,310, 4,794,028 and 4,872,243. The tool roller of these references which coacts with a second roller, is formed of a series of plates and defines a plurality of fastening element-forming cavities about its periphery. Similar tool rollers 103 are disclosed, for example, in U.S. Pat. Nos. 5,971,738, 5,900,350 and 5,875,527. U.S. Pat. No. 5,755,015 discloses an apparatus comprising a tool roller 103 adapted to be driven for one-way rotation and having in its circumferential surface a multiplicity of cavities and a molten resin supplying means such as a T-type die for supplying molten resin into a predetermined gap between the molten resin supplying means and the circumferential surface of the tool roller 103 while the latter is rotated. Suitable tool rollers 103 are disclosed, for example, in U.S. Pat. No. 5,690,875.

US 2002/090418 discloses an apparatus for continuously forming a thermoplastic web layer 13 bearing a plurality of male fastening elements 14 which comprises first and second rolls, a flexible mold belt defining an array of fastening element-shaped cavities extending from an outer surface thereof, the mold belt trained about both said rolls, and a source of molten plastic resin arranged to deliver the resin to the mold belt. The apparatus is constructed to force the plastic resin into the fastening element-shaped cavities of the belt under pressure in a gap to mold the array of fastening elements while forming the thermoplastic web layer. In the apparatus of US 2002/0190418, the tool roller 103 is thus essentially replaced by a mold belt.

The nip comprises another roll 101 which transports the fibrous web layer 11 into the nip and acts as a backup roller. The roll 101 preferably provides some pressure to assist in forcing the thermoplastic resin into the cavities and to laminate the fibrous web layer 11 and the thermoplastic web layer 13 to each other.

The interior of the tool roller 103 may be supplied with a vacuum equipment to assist in removal of air from the cavities 120 that may otherwise interfere with complete filling of such cavities.

Depending on the selection of the thermoplastic resin and the fibrous material it may be desirable to cool one or both of the roll 101 and the tool roll 103, and/or to heat the tool roll 103. Heating of the roll 101 is also possible but generally not preferred.

The amount of the thermoplastic resin injected into the nip is preferably selected so that the initial thickness of the thermoplastic web layer 13 is between 10 and 750 μm, more preferably between 20 and 500 μm and especially preferably between 20 and 300 μm. The thermoplastic web layer 13 preferably is essentially flat but it is also possible that a surface structure is imparted by means of roll 101 through the fibrous web layer 11. This may be desirable, for example, in order to improve the bonding between the thermoplastic web layer 13 and the fibrous web layer 11 by pushing the fibrous web layer 11 into the molten thermoplastic web layer 13. This can be obtained by using a roll 101 having a surface structure resulting in areas with higher nip pressures. It is also possible that the surface of the thermoplastic web layer 13 bearing a plurality of male fastening elements 14 comprises a structure in addition to the male fastening elements 14 which may also be imparted by the tool roll 103. In case the thermoplastic web layer 13 is not essentially flat but exhibits a surface structure in addition to the male fastening elements 14, the thickness values specified above reflect the average thickness of the thermoplastic web layer 13.

The surface of the thermoplastic web layer 13 which is opposite to the fibrous web layer 11, bears a multitude of male fastening elements 14. The male fastening elements 14 are integral with the surface of the thermoplastic web layer 13 and they are preferably composed of the same material as the thermoplastic web layer 13. In this case, one thermoplastic resin material is used and preferably injected into the nip using one or more dies. It is, however, also possible to use, for example, two different thermoplastic resin materials as was described above.

The form of the male fastening elements 14 which is determined by the shape and geometry of the cavities 20, can vary widely as was described above. The male fastening elements 14 preferably have a hook shape, and they usually comprise a stem supported by the surface of the thermoplastic web layer 13 opposite to the fibrous web layer 11, and an enlarged section which is positioned at the end of the stem opposite to the surface of the thermoplastic web layer 13 the stems are emanating from. The male fastening elements can also be formed by stems having no enlarged section at the end of the stem whereby such stems are preferably essentially conical, cylindrical or pyramidal. The shape of the male fastening elements 14 can also be modified after the precursor web laminate 10 has been stripped of the tool roll 103 by subjecting such elements to thermal, mechanical or radiation energy. In a preferred embodiment, the precursor web laminate 10 or the stretched mechanical fastening web laminate 1, respectively, is passed between two cylindrical rolls whereby the roll contacting the male fastening elements 14 is heated to modify the shape of the upper end of the stems. When passing, for example, a precursor web laminate 10 or a stretched mechanical fastening web laminate 1, respectively, having stems as mechanical fastening elements 14, by such heated roller, enlarged sections are formed at the upper end of the stems thereby creating mushroom-type mechanical fastening elements 14.

The enlarged section of the male fastening elements may have any shape such as hooks, T's, J's, mushroom-type heads (including concavely curved heads and disc-shaped heads) or any other shape allowing for engagement with complementary female fastening materials.

The dimensions of the individual male fastening elements 14 can be varied widely depending on the application and the structure and loftiness of the complementary female fastening material. When employing portions of the stretched mechanical fastening web laminate 1 of the present invention, for example, in disposable sanitary articles such as incontinence articles, diapers or napkins, the male fastening elements 14 comprising stems and, optionally, an enlarged section at the end of the stem preferably are between 40 μm and 2 mm in height above the surface of the thermoplastic web layer 13. The stems preferably have a cross-section with a maximum extension of between 10 μm and 250 μm. The ratio of the maximum extension of the enlarged portions of the male fastening elements 14 at the end of the stems over the maximum extension of the cross-sections of the stems preferably is between 1.5:1 and 5:1

The density of the cavities 120 in the tool roll 103 is preferably selected so that the average surface density of the male fastening elements 14 of the precursor web laminate 10 preferably is between $10/cm^2$ and $5,000/cm^2$, more preferably between $20/cm^2$ and $4,000/cm^2$ and especially preferably between $25/cm^2$ and $3,500/cm^2$ with respect to the surface of the precursor web laminate 10. The male fastening elements 14 may be distributed essentially uniformly on the thermoplastic web layer, or they may be arranged in regular pattern of any type or be distributed essentially randomly in order to vary the mechanical bonding properties of the stretched mechanical fastening web laminate with respect to a specific application. In a preferred pattern, the male fastening elements are arranged to form stripes in MD with the surface of the thermoplastic web layer 13 being exposed between such stripes.

The precursor web laminate 10 thus formed is then allowed to solidify at least partly and it is stripped from the tool roll 103.

In step (iii) of the first method of the present invention, the precursor web laminate 10 is stretched monoaxially or biaxially thereby decreasing the basis weight of the fibrous web layer 11 and the thickness of the thermoplastic web layer 13 from their initial values to provide a stretched mechanical fastening web laminate 1 having a basis weight of less than $100\ gm^{-2}$.

The term "biaxially stretched," when used herein to describe a stretched mechanical fastening web laminate 1, indicates that such stretched mechanical fastening web laminate 1 has been stretched in two different directions, a first direction and a second direction, in the plane of the stretched mechanical fastening web 1. Typically, but not always, the two directions are substantially perpendicular and are in the machine direction ("MD") of the precursor web laminate 10 and of its cross direction ("CD"). Unless context requires otherwise, the terms "orient," "draw," and "stretch" are used interchangeably throughout, as are the terms "oriented," "drawn," and "stretched," and the terms "orienting," "drawing," and "stretching." The term "transverse direction" is synonymous with and is used interchangeably with the term "cross direction". Biaxial stretching can be performed subsequently by stretching the precursor web laminate, for example, first in one of MD and CD and subsequently in the other of MD and CD. Stretching in each of the two directions can also be performed essentially simultaneously.

The term "monoaxially stretched" when used herein to describe a stretched mechanical fastening web laminate 1 indicates that stretching has been performed in one direction in the plane of such stretched mechanical fastening web 1. Typically such direction is one of MD and CD but other stretch directions are also possible.

The term "stretch ratio," as used herein to describe a method of stretching or a stretched mechanical fastening web laminate 1, indicates the ratio of a linear dimension of a given portion of a stretched mechanical fastening web laminate 1 to the linear dimension of the same portion prior to stretching. For example, in a stretched mechanical fastening web laminate 1 having an MD stretch ratio of 5:1, a given portion of the unstretched precursor web laminate 10 having a 1 cm linear measurement in the machine direction would have 5 cm measurement in the machine direction after stretch. In a stretched mechanical fastening web laminate 1 having a CD stretch ratio of 5:1, a given portion of unstretched precursor web laminate 10 having a 1 cm linear measurement in the cross direction would have 5 cm measurement in the cross direction after stretch.

The term "stretch parameter" is used to indicate the value of the stretch ratio minus 1. For example "first direction stretch parameter" and "second direction stretch parameter" are used herein to indicate the value of first direction stretch ratio minus 1, and second direction stretch ratio minus 1, respectively. Likewise, the terms "MD stretch parameter" and "CD stretch parameter" are used herein to indicate the value of MD stretch ratio minus 1, and CD stretch ratio minus 1, respectively. For example, an unstretched precursor web 10 that has not been stretched in the machine direction would have an MD stretch ratio of 1:1 (i.e., dimension after stretch is equal to dimension before stretch). Such an unstretched precursor web 10 would have an MD stretch parameter of 1 minus 1, or zero (i.e., the film has not been stretched). Likewise, a stretched mechanical fastening web laminate 1 having an MD stretch ratio of 7:1 would have an MD stretch parameter of 6:1.

In the example section below, both the stretch ratio in MD and CD, respectively, and an overall stretch ratio obtained by multiplying the MD and CD stretch ratio with each other, are reported.

When a precursor web laminates 10 is monoaxially or biaxially stretched at a temperature below the melting point of the polymer, particularly at a temperature below the line drawing temperature of the film, the precursor web laminate 10 may stretch non-uniformly, and a clear boundary is formed between stretched and unstretched parts. This phenomenon is referred to as necking or line drawing. Substantially the entire precursor web laminate 10 is stretched uniformly when it is stretched to a sufficiently high degree. The stretch ratio at which this occurs is referred to as the "natural stretch ratio" or "natural draw ratio." The necking phenomenon and the effect of natural stretch ratio is discussed, for example, in U.S. Pat. Nos. 3,903,234; 3,995,007; and 4,335,069 mostly for sequential biaxial orientation processes, i.e. where the first direction stretching and the second direction stretching are performed sequentially. When simultaneous equal biaxial stretching (also referred to as square stretching) is performed, the necking phenomena can be less pronounced, resulting in stretched areas having different local stretch ratios, rather than strictly stretched and unstretched parts. In such a situation, and in any simultaneous biaxial stretching process, the "natural stretch ratio" for a given direction is defined as that global stretch ratio at which the relative standard deviation of the local stretch ratios measured at a plurality of locations upon the stretched mechanical fastening web 1 is below about 15%. Stretching above the natural stretch ratio is widely understood to provide significantly more uniform properties or characteristics such as thickness, tensile strength, and modulus of elasticity. For any given precursor web laminate 10 and stretch conditions, the natural stretch ratio is determined by factors such as the composition of the thermoplastic resin forming the thermoplastic web layer 13 and the composition and initial basis weight of the fibrous web layer 11, morphology of the formed thermoplastic web layer 13 due to quenching conditions on the tool roll 103 and the like, and temperature and rate of stretching. Furthermore, for biaxially stretched mechanical fastening web laminates 1, the natural stretch ratio in one direction will be affected by the stretch conditions, including final stretch ratio, in the other direction. Thus, there may be said to be a natural stretch ratio in one direction given a fixed stretch ratio in the other, or, alternatively, there may be said to be a pair of stretch ratios (one in MD and one in CD) which result in the level of local stretch uniformity by which the natural stretch ratio is defined above.

Monoaxial stretching in MD can be performed by propelling the precursor web laminate 10 over rolls of increasing speed. The most versatile stretching method which allows for monoaxial, sequential biaxial and simultaneous biaxial stretching employs a flat film tenter apparatus. Such apparatus grasps the precursor web laminate 10 employing such means as a plurality of clips, grippers or other film edge-grasping means along opposing edges of the precursor web laminate 10 in such a way that monoaxial, sequential biaxial or simultaneous biaxial stretching in the desired direction is obtained by propelling the grasping means at varying speeds along divergent rails.

By increasing clip speed in the MD, stretch in the MD occurs. By using such means as diverging rails, CD stretch occurs. Such stretching can be accomplished, for example, by the methods and apparatus disclosed in U.S. Pat. Nos. 4,330,499 and 4,595,738, and more preferably by the methods and tenter apparatus disclosed in U.S. Pat. Nos. 4,675,582; 4,825,111; 4,853,602; 5,036,262; 5,051,225; and 5,072,493.

In the present invention stretching is preferably performed by means of flat film tenter stretching processes in order to minimize thickness variations. Flat film tenter stretching apparatuses are commercially available, for example, from Brückner Maschinenbau GmbH, Siegsdorf, Germany.

The precursor web laminate 10 of the present invention is preferably stretched in any of CD and MD independently from each other with a stretch ratio of between 1.5:1 and 10:1, more preferably between 1.5:1 and 7:1 and especially preferably between 1.5:1 and 5:1. The preferred stretch ratios apply independently from each other to both monoaxial and biaxial stretching with biaxial stretching being preferred.

Stretching is usually performed at elevated temperatures. Heating can be provided by IR irradiation, hot air treatment or by performing stretching in a heat chamber.

The stretched mechanical fastening web laminate 1 can be made flexible by suitable selection of the thermoplastic resin forming the male fastening elements 14 and the thermoplastic web layer 13, and/or by biaxially stretching the precursor web laminate 10.

Upon stretching, the thickness of the thermoplastic web layer 13 is decreased so that the ratio of the thickness of the thermoplastic web layer 13 of the precursor web laminate 10 prior to stretching to the thickness of the thermoplastic web layer 13 of the stretched mechanical fastening laminate 1 of the present invention preferably is between 3:1-40:1, more preferably between 5:1-30:1 and especially preferably between 5:1-25:1. The thickness of the thermoplastic web layer 13 of the stretched mechanical fastening web layer 13 of the stretched mechanical fastening web laminate 1 of the present invention is preferably between 5 and 200 μm and more preferably between 10 and 100 μm.

Also, upon stretching, the basis weight of the fibrous web layer 11 of the precursor web laminate 10 is decreased from its initial values prior to stretching so that the basis weight of the stretched mechanical fastening laminate 1 of the present invention is less than 100 $gm^{-2}$, preferably between 5-90 $gm^{-2}$, more preferably between 7-85 $gm^{-2}$ and especially preferably between 10-80 $gm^{-2}$. The ratio of the basis weight of the fibrous web layer 11 of the precursor web laminate 10 prior to stretching to the basis weight of the fibrous web layer 11 of the stretched mechanical fastening laminate 1 of the present invention preferably is between 3 and 40 and more preferably between 5 and 25.

Upon stretching the density of the male fastening elements 14 or the precursors is decreased and the distance between adjacent male fastening elements 14 or their precursors is increased so that the density of the male fastening elements 14 or their precursors preferably is between 1 and 2,500 $cm^2$, more preferably between 2 and 2,000 $cm^2$ and especially preferably between 5 and 1,800 $cm^2$. The ratio of the density of the male fastening elements 14 or the precursors with respect to the area of the precursor web laminate 10 prior to stretching, to the density of the male fastening elements 14 with respect to the area of the stretched mechanical fastening web laminate 1 upon stretching preferably is between 3:1 and 40:1, more preferably between 4:1 and 30:1 and especially preferably between 5:1 and 25:1.

Especially preferred are stretched mechanical fastening web laminates 1 having a density of the male fastening elements of between 2-200 $cm^{-2}$, more preferably between 4-150 $cm^{-2}$ and especially preferably between 5-80 $cm^{-2}$.

In certain applications, it has unexpectedly been discovered that very low densities of male fastening elements 14 are desirable. For example, hook densities of less than 100, preferably less than 70 and even less than 50 male fastening elements 14 per $cm^2$ are desirable when used to attach the stretched mechanical fastening web laminate 1 to low loft nonwoven materials. The low density of the male fastening elements 14 and, consequently, the increased spacing between adjacent fastening elements 14 has been found to increase the fastening efficiency of the individual fastening element 14.

Stretched mechanical fastening web laminates 1 having a density of the male fastening elements 14 of less than 100 can be advantageously used, for example, in large area fastening tabs of disposable diapers. The stretched mechanical fastening web laminate 1 has a size within such fastening tab of preferably from 5-100 $cm^2$ and more preferably of from 20-70 $cm^2$. It was found that such fastening tab can typically be directly attached to the back sheet of a diaper being formed of low loft nonwoven materials.

Stretched mechanical fastening web laminates 1 having a density of the male fastening elements 14 of less than 100 are also preferably used in feminine hygiene articles such as sanitary napkins. The stretched mechanical fastening web laminate 1 is preferably attached to the back sheet 52 and/or to side wrapping elements 54 of the sanitary napkin so that the patch of the stretched mechanical fastening web laminate 1 has a size within such sanitary napkin of preferably from 5-150 $cm^2$ and more preferably of 5-100 $cm^2$. It was found that such sanitary napkins are characterized by an increased wearer's comfort due to the low density of the male fastening elements 14 while still reliably anchoring it to essentially all undergarment materials.

It was surprisingly found by the present inventors that the shape of the mechanical fastening elements 14 or their precursors is not changed to an extent which would decrease the interaction between the stretched mechanical fastening web laminate 1 and a female fastening material which effectively cooperated with the precursor web laminate 10 prior to stretching, to a practically inacceptable degree upon stretching.

The stretched mechanical fastening web laminate 1 of the present invention has advantageous properties and, in particular, a high tensile strength in MD. The tensile strength at break of a stretched mechanical fastening web laminate 1 of the present invention as measured according to DIN EN ISO 527 having a certain value of the basis weight and a certain stretch ratio, preferably is, for example, higher than the tensile strength at break of a thermoplastic web layer 13 having the same basis weight and the same stretch ratio as such stretched mechanically fastening web laminate 1. The tensile strength at break of the stretched mechanical fastening web laminate 1 preferably is at least 10% and more preferably at least 15% increased in comparison to the tensile strength at break of a comparable thermoplastic web layer 13 having the same basis weight and exhibiting the same stretch ratio as such stretched mechanical fastening web laminate 1.

The stretched mechanical fastening web laminate 1 of the present invention also exhibits advantageous shear properties.

Stretched thermoplastic web layers 13 bearing a plurality of male fastening elements 14 on one of its major surfaces, also tend to create noise when being bent or flexed which especially disturbing, for example, in disposable hygiene products such as diapers or sanitary napkins. It was surprisingly found that the stretched mechanical fastening web laminate 1 of the present invention exhibits a distinctly reduced noise level in comparison to the stretched thermoplastic web layer 13 comprising a plurality of male fastening elements 14 comprising no fibrous web layer 11.

The present invention thus allows for manufacturing of low-weight and relatively thin stretched mechanical fastening web laminates 1 which exhibit advantageous mechanical properties and, in particular, a high mechanical strength. This can be seen, for example, from FIG. 5 which is a plot of the MD tensile strength at break for the stretched mechanical fastening web hooks of Example 1-2 (triangles), of the stretched hook web layers of Comparative Examples 1-2 (upright squares) and of Comparative Examples 3-4 (rotated squares), respectively, against the basis weight of such laminates and layers, respectively. For a given basis weight, the stretched mechanical fastening web laminate 1 of the present invention are characterized by superior mechanical properties and, in particular, by an increased MD tensile strength at break in comparison to stretched hook web layers having the same basis weight. The stretched mechanical fastening web laminates 1 of the present invention also exhibit advantageous mechanical properties and, in particular, an increased tensile strength at break in comparison to unstretched precursor web laminates 10 having the same basis weight.

The increased mechanical strength of the stretched mechanical fastening web laminate 1 of the present invention provides a better handleability during processing and allows to use thinner layers in comparison to hook web layers or unstretched precursor web laminates having the same mechanical properties. The advanced mechanical properties of the stretched mechanical fastening laminates of the present invention make them suitable, in particular, for use in disposable absorbent articles such as diapers or sanitary napkins.

It should be noted that the stretched mechanical fastening web laminate 1 can be manufactured by other methods than the preferred method disclosed above. It is, for example, also possible to first manufacture a thermoplastic web layer 13 comprising male fastening elements 14 (=collectively hook web layer), laminate a fibrous web layer 11 to the major surface of the thermoplastic web layer 13 which is opposite to the male fastening elements 14 and subject the resulting precursor web laminate 10 to stretching to provide the stretched mechanical fastening web laminate 1 of the present invention. U.S. Pat. No. 4,894,060, for example, discloses a method of preparing so-called profile extruded hooks which are obtained by extruding a thermoplastic web layer 13 bearing, for example, elongate spaced ribs projecting from a first major surface of the thermoplastic web layer 13. The ribs form a precursor of the male fastening elements and exhibit the cross-sectional shape of the hooks to be formed. U.S. Pat. No. 4,894,060 discloses in col. 7. lns. 44-62 a specific example of preparing a thermoplastic web layer bearing a rib. This passage is included herein by reference as an example of forming a precursor thermoplastic web layer 13 bearing a precursor of the male fastening elements. In a preferred second method of the present invention, the thermoplastic web layer 13 comprising spaced ribs is extrusion laminated to the fibrous web layer 13 thus forming a precursor web laminate 10. The ribs of the thermoplastic web layer 13 are then transversely cut or slit at spaced locations along the extension of the rib to form discrete portions of the rib having lengths in the direction of the rib essentially corresponding to the length of the male fastening elements 14 to be formed. Slitting of the ribs is exemplified in col. 7, lns. 63 68 which passage is herewith incorporated by reference. The precursor web laminate is subsequently stretched monoaxially or biaxially to provide the stretched mechanical fastening web laminate 1 of the present invention. The cross-sectional of shape of the ribs can be varied widely to adapt and optimize the cross-sectional shape the resulting male fastening elements 14 with respect to the specific application. It is also possible, for example, to use a sequence of ribs having different cross-sectional shapes. The profile extruded hooks disclosed in U.S. Pat. No. 4,894,060 may exhibit a rounded edging of the heads of the male fastening elements 14 and are preferably designed to have peel and shear values highest in CD as opposed to MD.

Alternatively, the fibrous web layer 11 can be attached in a third method according to the present invention to the thermoplastic web layer 13 of such hook web layer by an adhesive layer using, in particular, a pressure-sensitive adhesive. Suitable pressure-sensitive adhesives include rubber-based or acrylate-based pressure-sensitive adhesive materials. The stretched mechanical fastening web laminate 1 is subject matter of the present invention independently from the specific method of manufacturing applied.

The stretched mechanical fastening web laminate 1 of the present invention is suitable for various technical applications, and it is especially preferably used in disposable absorbent articles such as sanitary napkins or diapers.

The term sanitary napkin 50 as used above and below refers to an article which is worn by females adjacent to the pudential region that is intended to absorb and contain the various exudates which are discharged from the body (e. g. blood, menses and urine). The term sanitary napkin 50 is also meant to include light weight incontinence pads for adults. Sanitary napkins 50 typically have a top sheet 51 which provides a liquid pervious body-contacting surface and a back sheet 52 which provides a liquid impervious garment surface. The top sheet 51 and the back sheet 52 preferably sandwich an absorbent core 53 providing the means for absorbing menses and other body fluids. The top sheet 51 is intended to be worn adjacent to the body of the wearer. The back sheet 52 of the sanitary napkin is on the opposite side and is intended to be placed adjacent to the wearer's undergarments when the sanitary napkin 50 is worn.

Constructions of sanitary napkins 50 are described in detail, for example, in U.S. Pat. No. 5,611,790, WO 98/53,782, U.S. Pat. No. 5,778,457, U.S. Pat. No. 6,039,712, WO 98/53,781, U.S. Pat. Nos. 4,336,804, 4,475,913, 6,443,932 and 5,507,735.

The present invention, however, is not limited to the particular types or configurations of sanitary napkins 50 described in the above references.

Figure 3A:
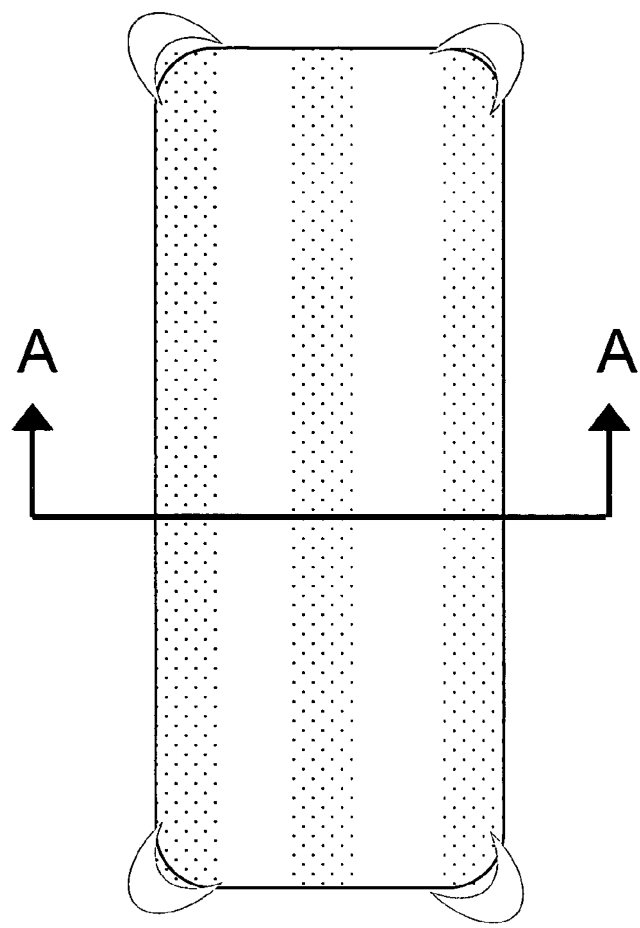
FIG. 3*a* is a top view on the back sheet 52 of a sanitary napkin of the present invention, said back sheet 52 being composed of a portion of the stretched mechanical fastening web laminate 1 of the present invention.

The sanitary napkins 50 according to the present invention differ from prior art constructions in that the back sheet 52 comprises a portion of a stretched mechanical fastening web laminate 1 of the present invention. FIG. 3*a* shows a schematic top-view of the back sheet 52 of a sanitary napkin 50 wherein such back sheet 52 is composed of a portion of the stretched mechanical fastening web laminate 1 of the present invention. It can be seen from the schematic cross-sectional view of FIG. 3*b* along the line indicated in FIG. 3*a* that the back sheet 1, 52 comprises a thermoplastic web layer 13 bearing a multitude of male fastening elements 14 of the mushroom hook type in a striped arrangement. The male fastening elements 14 are arranged in three strip-shaped areas in the direction of the longitudinal axis of the sanitary napkin, and the thermoplastic web layer 13 is exposed in the strip-shaped areas between the male fastening elements 14.

The sanitary napkin 50 of FIGS. 3*a, b* is to illustrate a preferred use of the stretched mechanical fastening web 1 of the present invention without limiting it.

While in the embodiment of FIGS. 3*a, b* the back sheet 52 of the sanitary napkin 50 is composed of a portion of the stretched mechanical fastening web 1, it is also possible that one or more portions of such stretched mechanical fastening web laminate 1 are subsequently attached, for example, by adhesive, thermal or ultrasonic bonding, to an underlying back sheet 52 of a sanitary napkin 50. It is also possible, for example, that one or more portions of the stretched mechanical fastening web laminate 1 are applied to only part of the back sheet 52 so that part of the back sheet 52 remains exposed. The sanitary napkin may comprise, for example, side wrapping elements 54 as is schematically illustrated in FIGS. 4*a, b*. It is also possible that the male fastening elements 14 of the portions of the stretched mechanical fastening web 1 exhibit a pressure-sensitive adhesive on the top portions of the heads of the male fastening elements 14 as is described, for example, in EP 0,894,448, and/or on at least part of the interstitial spaces between the male fastening elements 14 as is described, for example, in U.S. Pat. No. 4,959,245, in order to provide for a combination of a mechanical and an adhesive bonding mechanism. Alternatively, in case the back sheet 52 exhibits areas which are free of male fastening elements 14 like, for example, in the embodiments of the sanitary napkins of FIGS. 3 and 4, pressure-sensitive adhesive may be arranged in such areas free of male fastening elements 14.

The stretched mechanical fastening web 1 of the present invention exhibits a low or relatively low thickness and a low basis weight in combination with an advantageous mechanical strength. The shape and density of the male fastening elements 14 can be varied so that a sanitary napkin 50 having a back sheet 52 comprising one or more portions of a stretched mechanical fastening web 1, can be reliably secured to a variety of undergarments comprising various fibrous materials such as woven, knitted or nonwoven materials comprising, for example, cotton, silk, nylon, polyester, polyolefin such as polypropylene or any mixture of the preceding materials.

The sanitary napkins of the present invention are thus characterized by a high reliability, an increased mechanical strength resulting in an improved handleability, and—due to the low or relatively low thickness of the stretched mechanical fastening web laminate 1—increased wearer's comfort.

Portions of the stretched mechanical fastening web laminate 1 of the present invention may also be used, for example, in diapers.

DETAILED DESCRIPTION OF THE FIGURES

Figure 1B:
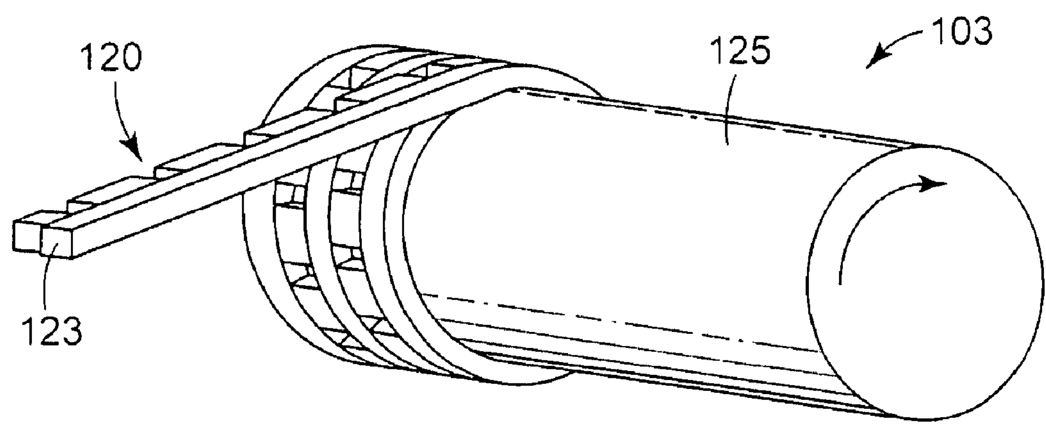
FIG. 1*b* schematically shows a method of manufacturing a cylindrical roll comprising cavities 120 (referred to above and below as tool roll 103) which is suitable in the method of the present invention.
Figure 1C:
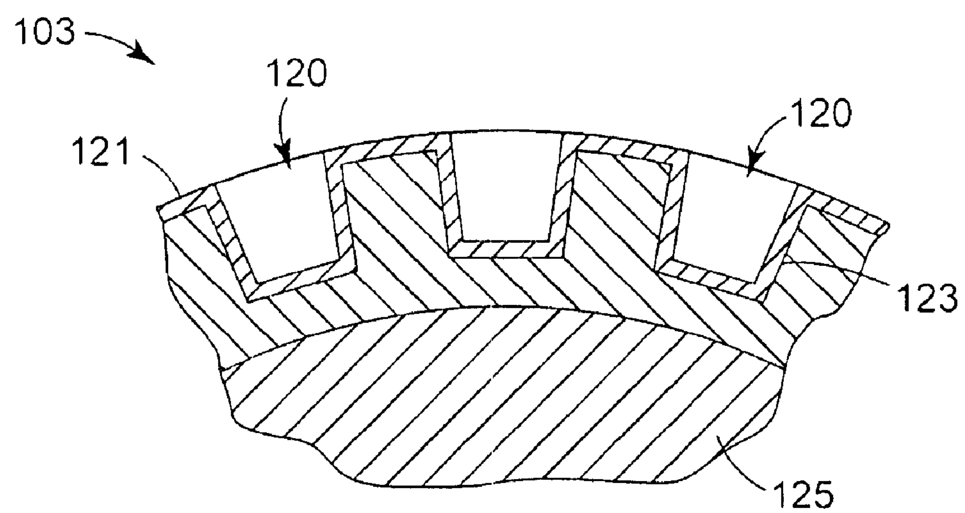
FIG. 1*c* is an enlarged cross-sectional view of the tool roll 103 obtained by the method shown in FIG. 1*b*.

FIG. 1*a* shows an apparatus 100 and a method for producing a precursor web laminate 10 useful in the present invention. The apparatus comprises an extruder 102 introducing a molten thermoplastic resin through its die 104 into a nip formed by the tool roll 103 and the roll 101. The roll 101 transports the fibrous web layer 11 into the nip. The molten thermoplastic resin is introduced into the cavities 120 of the tool roll 103 in an excess of an amount that would fill the cavities 120 so that a thermoplastic web layer 13 is formed which is attached to the fibrous web layer 11. The thermoplastic resin is then solidified and the precursor web laminate 10 comprising a fibrous web layer 11 and a thermoplastic web layer 13 bearing a multitude of male fastening elements 14 is stripped from the tool roll 103.

FIG. 1*b* schematically shows a method of preparing a tool roll 103 comprising winding a wire 123 comprising cavities 120 onto a cylindrical base roll 125.

FIG. 1*c* schematically shows a cross-sectional view through the tool roll 103. The wire 123 comprises cavities 120, and the exposed surface of the wire 123 exhibits a coating 121.

Figure 2:
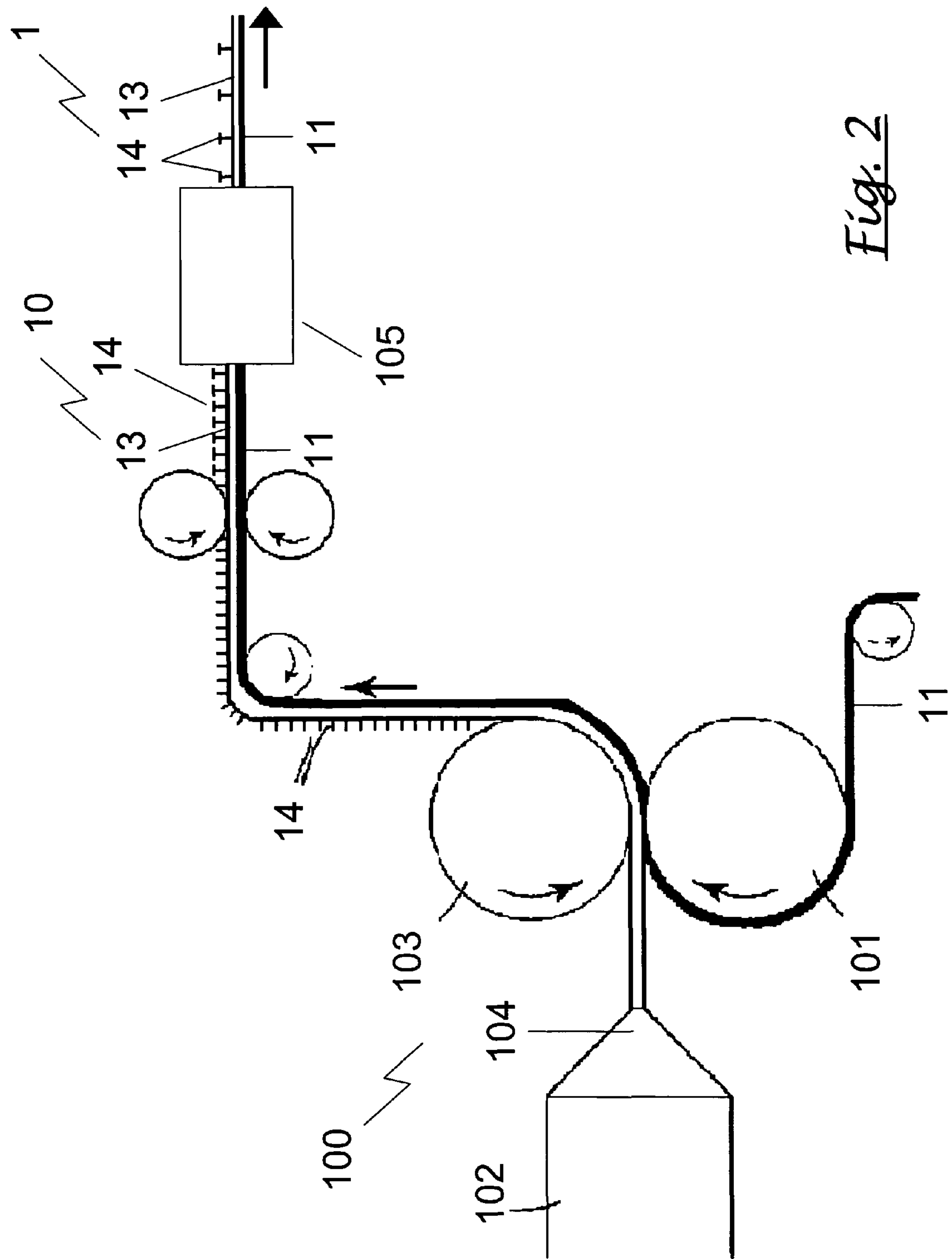
FIG. 2 schematically shows an apparatus 150 suitable for making a stretched mechanical fastening web laminate 1 of the present invention.

FIG. 2 schematically shows an apparatus 150 and a method for manufacturing a stretched mechanical fastening web 1 of the present invention. The apparatus comprises the apparatus 100 for manufacturing the precursor web laminate 10 and an apparatus 105 for stretching the precursor web laminate.

FIG. 3*a* schematically shows a top view on the back sheet 52 of a sanitary napkin 50 of the present invention where such back sheet 52 is composed of a portion of the stretched mechanical fastening web 1 of the present invention. The male fastening elements 14 of such web 1 are arranged in strip-like areas in the direction of the longitudinal axis (MD) of the sanitary napkin 50 while the areas between such strip-shaped areas are free of male fastening elements 14.

Figure 3B:
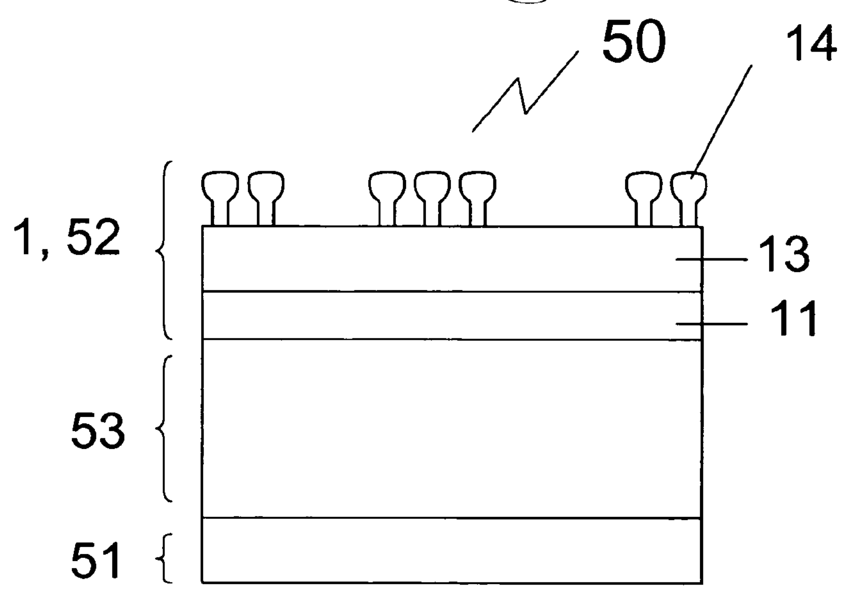
FIG. 3*b* is a cross-sectional view of the sanitary napkin 50 of FIG. 3*a* along the line A-A.
Figure 4A:
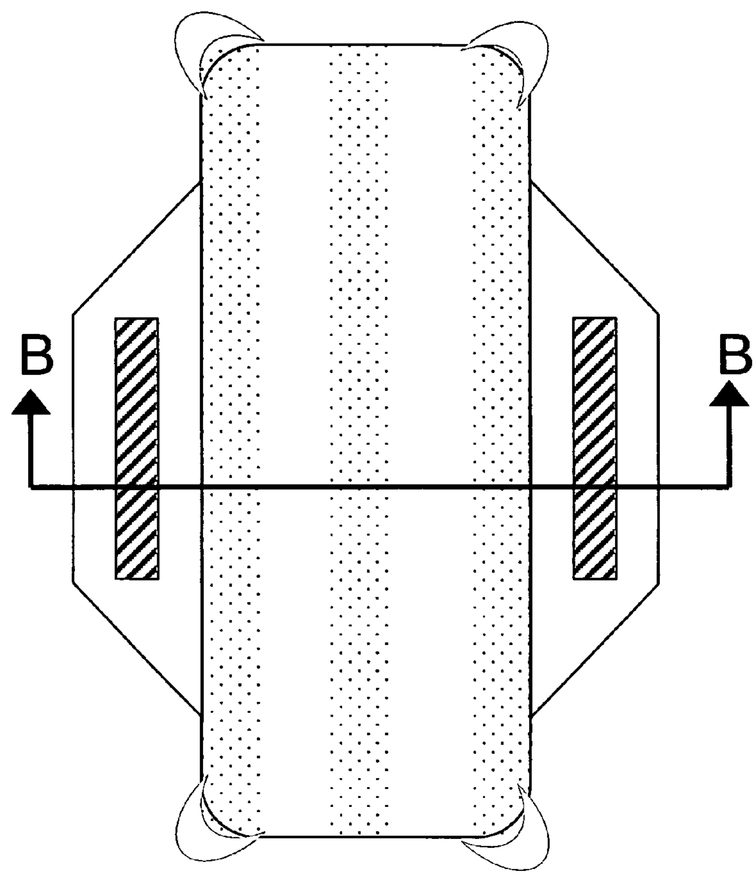
FIG. 4*a* is a top view on the back sheet 52 of another sanitary napkin of the present invention, said back sheet 52 being composed of a portion of the stretched mechanical fastening web laminate 1 of the present invention.

FIG. 3*b* is a cross-sectional view along the line A-A through the sanitary napkin 50. The sanitary napkin comprises an absorbent core 53 sandwiched between top sheet 51 and back sheet 52 which is composed of a portion of the stretched mechanical fastening web 1 of the present invention. Such portion of the web 1 comprises a fibrous web layer 11 and a thermoplastic web layer 13 bearing a multitude of male fastening elements 14 which are arranged in strip-shaped areas in CD.

FIG. 4*a* is a top view of the back sheet 52 of the sanitary napkin of FIGS. 3*a, b* additionally comprising side wrapping elements 54. The side wrapping elements comprise a film 55 attached to the top sheet 51 of the sanitary napkin 50. The film 55 bears on its major surface facing towards the back sheet 52, a secondary attaching means 56 such as a pressure-sensitive adhesive layer.

Figure 4B:
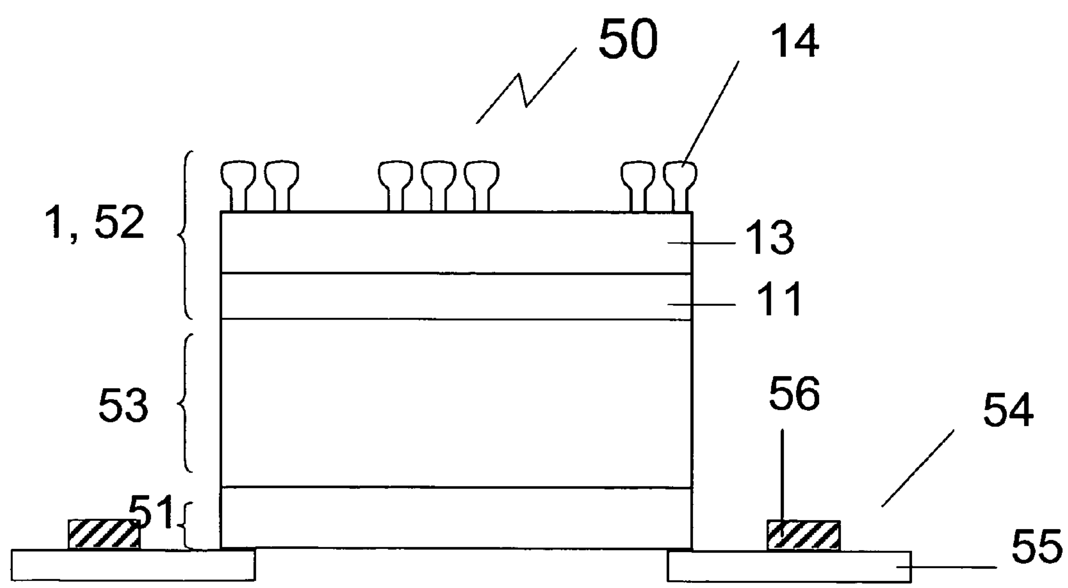
FIG. 4*b* is a cross-sectional view of the sanitary napkin 50 of FIG. 4*a* along the line B-B.

FIG. 4*b* is a cross-sectional view along the line B-B through the sanitary napkin 50.

Figure 5:
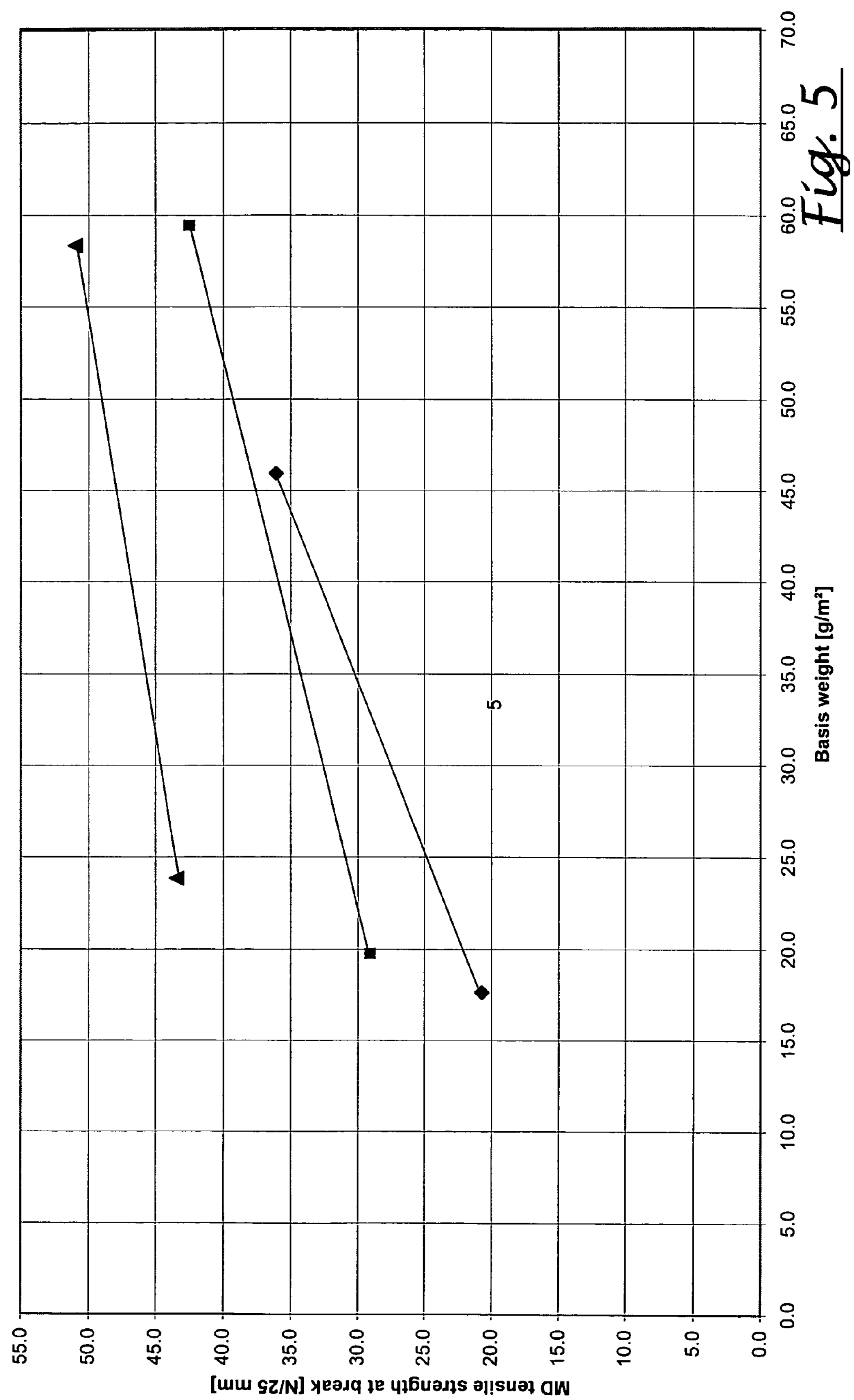
FIG. 5 is a plot of the MD tensile strength at break for the stretched mechanical fastening web hooks of Example 1-2 (triangles), of the stretched hook web layers of Comparative Examples 1-2 (upright squares) and of Comparative Examples 3-4 (rotated squares), respectively, against the basis weight of such laminates and layers, respectively.

FIG. 5 is a plot of the MD tensile strength at break for the stretched mechanical fastening web hooks of Example 1-2 (triangles), of the stretched hook web layers of Comparative Examples 1-2 (upright squares) and of Comparative Examples 3-4 (rotated squares), respectively, against the basis weight of such laminates and layers, respectively.

The present invention will be further described by the following examples which are to illustrate the invention without limiting it. Prior to this, some test methods are described which will be used in the examples.

Materials Used in the Examples

Resins for manufacturing fibrous web layers 11

FINATHENE 3868

A polypropylene copolymer having a melt flow index MFI of 37 and a density of 0.905 g/cm$^3$, available from Atofina, Houston/Tex., USA

FINATHENE 3825

A polypropylene copolymer having a melt flow index MFI of 30 and a density of 0.905 g/cm$^3$, available from Atofina, Houston/Tex., USA.

FINAPLAS 1571

A syndiotactic polypropylene having a melt flow index MFI of 10 and a density of 0.87 g/cm$^3$, available from Atofina, Houston/Tex., USA Blend 1

Consists of 80% FINATHENE 3868 and 20% FINAPLAS 1571, both available from Atofina, Houston/Tex., USA. Density: 0.902 g/cm$^3$ Blend 2

Consists of 90% FINATHENE 3868 and 10% FINAPLAS 1571, both available from Atofina, Houston/Tex., USA. Density: 0.906 g/cm$^3$ Thermoplastic Resins for Producing the Thermoplastic Web Layer 13

DOW 7C05N

Polypropylene having a melt flow index of 15 and a flexural modulus of 1230 MPa, available from Dow Chemicals Company, Midland/Mich., USA.

Prefabricated Fibrous Web Layers 11

AMOCO RFX

Nonwoven spunbond fibrous web comprising polypropylene resin filaments; web weight 16.9 g/m$^2$ commercially available from Amoco Corp., Chicago, Ill., U.S.A.

Thermoplastic Hook Web Layers

These thermoplastic web layers 13 comprising male fastening elements which are referred to above and below as hook web layers, are tested for comparative purposes.

Hook Web Layer 1

Thermoplastic web comprising hook-shaped male fastening elements 14 having a web weight of 110 g/m$^2$ and a hook density of 248 cm$^{-2}$; commercially available from 3M Company, St. Paul/Minn., USA as type KHK-0001 hook web layer.

Hook Web Layer 2

Thermoplastic web comprising hook-shaped male fastening elements 14 having a web weight of 139 g/m$^2$ and a hook density of 217 cm$^{-2}$; commercially available from 3M Company, St. Paul/Minn., USA as type KHK-0004 hook web layer.

Test Methods

Tensile Strength in Machine Direction at Break (MD-Tensile Strength at Break)

The MD-tensile strength at break was tested according to the DIN EN ISO 527-1, where a portion of the respective web layer or web laminate, respectively, to be tested, was elongated in MD (which corresponded to the direction of the largest extension of the portion) at constant speed of 500 mm/min until breakage was reached. While DIN EN ISO 527-1 specifies that the test is repeated for 5 different portions with the results being averaged, only 3 portions were evaluated in each case in the present invention and the results were averaged. The results are reported in N/25.4 mm.

Filament Titer

The fiber titer in denier was calculated from the average diameter of the filaments and the densities of the polymer used for manufacturing the nonwoven fibrous web layer 11 applying the following formula.

$$\text{titer [den]}=(\text{diameter of the filament in } \mu\text{m})^2\times 0.007068\times\text{density of the polymer } [(\text{g/cm}^3)]$$

The average diameter of the filaments was measured using a Nikon Eclipse E600 polarized microscope manufactured by Nikon Instruments Inc, 1300 Walt Whitman Road, Melville, N.Y. The microscope was carefully aligned to center objectives, optics, condenser and light source. Then a filament to be measured was placed into the center of the view field focusing the image on the widest section of the filament. The diameter of the filament is then measured using a calibrated scale. The average diameter of the filament was obtained using a minimum of 25 measurements of different filaments. The density of the polymer used for producing the fibrous web layer 11 is given in the material section above.

Basis Weight of Web Layers and Web Laminates, Respectively

A rectangular portion of the respective web laminate or web layer, respectively, was cut to the dimensions of about 5×5 cm$^2$. The weight of the samples was obtained by using a SARTORIUS L 420 P type balance. The weight was measured 3 times (with a sensibility of mg) and averaged. The basis weight of the web layers and web laminates, respectively, was obtained as the ratio of the weight of the portion over its surface area and is reported in g/m$^2$.

Caliper of the Web Layers and Web Laminates, Respectively, and Surface Density of the Male Fastening Elements 14

The caliper of the web layers and web laminates, respectively, were measured by using a MITOTOYO TM 176-811D microscope. The microscope exhibited a graticule, and the microscope plate was movable in CD and MD. The displacement in MD and CD was measured using two adjusting screws, and the respective displacement could be read from a digital display with an accuracy in the range of μm. The caliper of the thermoplastic web layer 13 and the height of the male fastening elements 15 were measured in sectional view.

In order to obtain the density of the male fastening elements 14, the plate of the microscope was displaced so that at least 15 different male fastening elements could be counted. The density of the male fastening elements 15 was obtained as the ratio of the number of male fastening elements 15 over the area covered by the movable plate of the microscope.

The values reported are average values obtained in each case from 6 different measurements.

Stretch Ratio

The stretch ratio of the stretched mechanical fastening web laminate 1 with respect to the precursor web laminate 10 was obtained by dividing the density of the male fastening elements 14 of the unstretched precursor web laminate 10 by the density of the male fastening elements 14 of the stretched mechanical fastening web laminate 1. The density of the male fastening elements 14 was measured in each case by counting the male fastening elements 14 along an appropriate distance of at least 20 mm in MD and CD, respectively. The resulting values are reported as stretch ratios in MD and CD, respectively, and as an overall stretch ratio MD*CD obtained by multiplying the respective stretch ratios in MD and CD, respectively.

Elongation at Break

The elongation at break was measured according to DIN EN ISO 527. The elongation at break was reported in [%]

Spinning Speed

The spinning speed was calculated by the output of the spinneret in g/hole·min and the fiber titer. The spinning speed was obtained by the following formula:

$$\frac{\text{output} \cdot 9000}{\text{fiber titer } (den)}$$

The resulting values are reported in m/min.

EXAMPLES

Examples 1, 2 and Comparative Examples 1-4

Example 1

A prefabricated fibrous web of the type Amoco RFX which was arranged in 3 tiers, was provided and fed into the nip between a base roll 101 and a tool roll 103 at a speed of 11 m/min. The roll 101 had a silicone rubber surface, and the tool roll 103 comprised cavities 120 for forming pin-type male fastening elements at a density specified in table 1 below. The cavities 120 of the tool roll 103 were shaped to provide pin-type mechanical fastening elements having a height of 446 μm. The two rolls 101, 103 had a circumference of 72 cm (roll 101) and 144 cm (roll 103), and a width of about 30 cm.

Thermoplastic resin DOW 7C05N was extruded and fed in a molten state through die 104 at a temperature of 450° F. (232° C.) into the nip. The nip pressure and nip gap was adjusted so that the thermoplastic web layer 13 formed had a caliper (measured without male fastening elements 14) of about 97 μm. When forming with these adjustments a thermoplastic web layer 13 comprising male fastening elements 14 without feeding a fibrous layer into the nip, the resulting hook web layer had a basis weight of 113.8 g/m$^2$. During the manufacturing of the precursor web laminate 10, the tool roll 103 was held at an essentially constant temperature of 175° F. (79° C.), and the temperature of the base roll 101 was adjusted to an essentially constant value of 40° F. (4° C.).

By passing the nip between the two rollers 101, 103 the molten thermoplastic resin solidified sufficiently so that it could be stripped off from the tool roll 103 to provide the precursor web laminate 10.

Stretching of the precursor web laminate 10 was performed in a tenter frame stretching apparatus 105 commercially available from Brückner Maschinenbau GmbH, Siegsdorf, Germany under the trade designation Karo IV. A portion of the precursor web laminate was simultaneously biaxially stretched in MD and CD at an overall stretch ratio of 2.7:1. using a stretching speed of 10%/second in each direction. Stretching was performed at a temperature of 151° C. after conditioning the samples at 151° C. for 60 sec.

The density of the male fastening elements 14 before and after stretching, the stretch ratios in MD and CD, the overall stretch ratio MD*CD, the basis weight of the precursor web laminate 10 and of the stretched mechanical fastening web laminate 1, and the MD-strength at break and the elongation at break of the stretched mechanical fastening web laminate 1 were measured as described above.

Example 2

Example 1 was repeated with the difference that the precursor web laminate 10 was simultaneously biaxially stretched at a stretch ratio of 6.4:1.

The density of the male fastening elements 14 before and after stretching, the stretch ratios in MD and CD, the overall stretch ratio MD*CD, the basis weight of the precursor web laminate 10 and of the stretched mechanical fastening web laminate 1, and the MD-strength at break and the elongation at break of the stretched mechanical fastening web laminate 1 were measured as described above.

The MD tensile strength at break of the stretched mechanical fastening web laminates 1 of Examples 1 and 2 are plotted as a function of the base weight of the stretched mechanical fastening web laminate 1 in FIG. 5 (triangles). The MD tensile strength at break vs. the base weight of the stretched hook web layers of Comparative Examples 1-2 (upright squares) and Comparative Examples 3-4 (rotated squares) is plotted in FIG. 5 for comparison as well.

It can be seen that the stretched mechanical fastening web laminate 1 of the present invention offers distinctly higher values of the MD tensile strength at break than hook web layers for the same basis weight of the respective material.

Comparative Example 1

A portion of hook web layer 1 described in the material section above sample was simultaneously biaxially stretched in MD and CD at a stretching speed of 10%/second in each direction to provide a stretch ratio of 2.4:1. Stretching was performed at a temperature of between 149-153° C. after conditioning the samples at such temperatures for 60 sec. Prior to stretching, the portion of the hook layer had been conditioned for 60 seconds in an oven at temperatures of between 149° C. and 153° C. Stretching of the portion of the hook web layer 1 was performed in a tenter frame stretching apparatus 105 commercially available from Brückner Maschinenbau GmbH, Siegsdorf, Germany under the trade designation Karo IV as described in Example 1 above.

The density of the male fastening elements 14 before and after stretching, the stretch ratios in MD and CD, the overall stretch ratio MD*CD, the basis weight of the precursor web laminate 10 and of the stretched mechanical fastening web laminate 1, and the MD-strength at break and the elongation at break of the stretched mechanical fastening web laminate 1 were measured as described above.

Comparative Example 2

A portion of hook web layer 1 was simultaneously biaxially stretched as described in Comparative Example 1 above applying a stretch ratio of 6.1:1.

The density of the male fastening elements 14 before and after stretching, the stretch ratios in MD and CD, the overall stretch ratio MD*CD, the basis weight of the precursor web laminate 10 and of the stretched mechanical fastening web laminate 1, and the MD-strength at break and the elongation at break of the stretched mechanical fastening web laminate 1 were measured as described above.

Comparative Examples 3 and 4

Comparative Example 1 was repeated by using the hook web layer 2 and applying a stretch ratio of 2.3:1 and 7.2:1, respectively.

The density of the male fastening elements 14 before and after stretching, the stretch ratios in MD and CD, the overall stretch ratio MD*CD, the basis weight of the precursor web laminate 10 and of the stretched mechanical fastening web laminate 1, and the MD-strength at break and the elongation at break of the stretched mechanical fastening web laminate 1 were measured as described above.

The fibrous web layer 11 obtained was thermally bonded using a two calendar rolls having a square bond pattern with 20% bond area. The calendar rolls were held at a temperature of 149° C. and operated at a pressure of 30 psi (206.8 kPa).

The basis weight of the spunbond fibrous web layer 11 was varied by changing the speed of the conveyor belt forming the support for the fibrous web layer exiting from the spinneret. The basis weights of the precursor web laminate 10 with the calandered fibrous web layer 11 obtained in Examples 3-5 are summarized in table 2 below. The fibrous layer was stored for a maximum of 2 hours before laminating it to the thermoplastic web layer 13.

The formation of the thermoplastic web layer bearing male fastening elements 14 was performed as described in Example 1 above by feeding the calandered fibrous web layer 11 into the nip between the two rollers 101, 103. The molten thermoplastic resin solidified and thus bonded to the fibrous web layer 11 so that it could be stripped off from the tool roll 103 to provide the precursor web laminate 10.

The precursor web laminate 10 was simultaneously biaxially stretched as described in Example 1 above adjusting the stretch ratios given in table 2 below.

The density of the male fastening elements 14 before and after stretching, the stretch ratios in MD and CD, the overall stretch ratio MD*CD, the basis weight of the precursor web laminate 10 and of the stretched mechanical fastening web laminate 1, and the MD-strength at break and the elongation at break of the stretched mechanical fastening web laminate 1 were measured as described above.

TABLE 1

Examples 1, 2 and Comparative Examples 1-4

| | Example 1 | Example 2 | Comparative Example 1 | Comparative Example 2 | Comparative Example 3 | Comparative Example 4 |
|---|---|---|---|---|---|---|
| Density of male fastening elements before stretching [cm$^{-2}$] | 216 | 216 | 248 | 248 | 217 | 217 |
| Density of male fastening elements after stretching [cm$^{-2}$] | 80 | 34 | 103 | 41 | 94 | 30 |
| Overall stretch ratio [stretch ratio in MD * stretch ratio in CD] | 2.7:1 (1.64 * 1.64) | 6.4:1 (2.53 * 2.53) | 2.4:1 (1.55 * 1.55) | 6.1:1 (2.47 * 2.47) | 2.3:1 (1.52 * 1.52) | 7.2:1 (2.68 * 2.68) |
| Basis weight of precursor web laminate [g/m$^2$] | 162 | 162 | 110 | 110 | 139 | 139 |
| Basis weight of stretched mechanical fastening web laminate [g/m$^2$] | 58 | 24 | 46 | 18 | 60 | 20 |
| MD-strength at break of the stretched mechanical fastening web laminate or stretched hook web layer, respectively [N/25 mm] | 51.0 | 43.4 | 36.1 | 20.7 | 42.5 | 29.1 |
| Elongation at break of the stretched mechanical fastening web laminate or stretched hook web layer, respectively [%] | 38 | 40 | 112 | 84 | 167 | 89 |

Examples 3-5

In this Example 3, a spunbond nonwoven fibrous web was manufactured. Resin FINATHENE 3825 was processed in an extruder at a temperature of 245° C. and spun through the extrusion head (spinneret) having a total of 512 orifices (16 rows of orifices with each row having 32 orifices). The die had a transverse length of 7.875 inches (200 millimeters). The diameter of each orifice was 0.889 mm and the L/D ratio (=length/diameter) of each orifice was 6. The polymer flow rate was 0.66 g/(hole*min). The cooling air at the spinneret had a temperature of 45° F. (7° C.). The average titer of the filaments obtained was 3.3 den.

TABLE 2

Examples 3-5

| | Example 3 | Example 4 | Example 5 |
|---|---|---|---|
| Density of male fastening elements before stretching [cm$^{-2}$] | 216 | 216 | 216 |

TABLE 2-continued

| Examples 3-5 | | | |
|---|---|---|---|
| | Example 3 | Example 4 | Example 5 |
| Density of male fastening elements after stretching [$cm^{-2}$] | 75 | 50 | 41 |
| Overall stretch ratio [stretch ratio in MD * stretch ratio in CD] | 2.8:1 (1.67 * 1.67) | 4.4:1 (2.10 * 2.10) | 5.3:1 (2.30 * 2.30) |
| Basis weight of precursor web laminate [$g/m^2$] | 212 | 212 | 212 |
| Basis weight of stretched mechanical fastening web laminate [$g/m^2$] | 66 | 46 | 39 |
| MD tensile strength at break [N/25 mm] | 79.2 | 69.2 | 55.5 |

Examples 6-9

Example 3 was repeated using FINATHENE 3868 resin instead of FINATHENE 3825. The filament titer obtained was 2.3 den.

The fibrous web layer obtained was not calandared. The basis weight of the precursor web laminate 10 was varied by varying the speed of the supporting conveyor belt as was described in Example 3; the values of the basis weight are reported in table 3. The precursor web laminate was biaxially stretched as described in Example 3 varying the stretch ratio as indicated in table 3 below.

The density of the male fastening elements 14 before and after stretching, the stretch ratios in MD and CD, the overall stretch ratio MD*CD, the basis weight of the precursor web laminate 10 and of the stretched mechanical fastening web laminate 1, and the MD-strength at break and the elongation at break of the stretched mechanical fastening web laminate 1 were measured as described above.

TABLE 3

| Examples 6-9 | | | | |
|---|---|---|---|---|
| | Example | | | |
| | 6 | 7 | 8 | 9 |
| Density of male fastening elements before stretching [$cm^{-2}$] | 216 | 216 | 216 | 216 |
| Density of male fastening elements after stretching [$cm^{-2}$] | 86 | 70 | 33 | 71 |
| Basis weight of precursor web laminate [$g/m^2$] | 165 | 172 | 172 | 199 |
| Overall stretch ratio [stretch ratio in MD * stretch ratio in CD] | 2.5:1 (1.59 * 1.59) | 3.07:1 (1.75 * 1.75) | 6.45:1 (2.54 * 2.54) | 3.04:1 (1.75 * 1.75) |
| MD tensile strength at break of the stretched mechanical fastening web laminate [N/25 mm] | 52.1 | 72.2 | 44.3 | 76.4 |
| Basis weight of fibrous web layer 11 before stretching [$g/m^2$] | 30 | 50 | 50 | 70 |
| Basis weight of stretched mechanical fastening web laminate [$g/m^2$] | 43 | 50 | 26 | 63 |

Example 10

Example 3 was repeated using Blend 1 described in the material section above as a resin instead of FINATHENE 3825. The polymer flow rate was 0.44 g/(hole*min) and the filament titer obtained was 2.8 den.

The fibrous web layer was taken up by a conveyor belt running at 1414 m/min and was calendar-bonded as described in Example 3.

The basis weight of the spunbond fibrous web layer 11 which was calandered as described in Example 3, was 30 g/m$^2$.

The density of the male fastening elements 14 before and after stretching, the stretch ratios in MD and CD, the overall stretch ratio MD*CD, the basis weight of the precursor web laminate 10 and of the stretched mechanical fastening web laminate 1, and the MD-strength at break and the elongation at break of the stretched mechanical fastening web laminate 1 were measured as described above.

TABLE 4

Example 10

| | Example 10 |
|---|---|
| Density of male fastening elements before stretching [cm$^{-2}$] | 216 |
| Density of male fastening elements after stretching of stretched mechanical fastening web laminate [cm$^{-2}$] | 84 |
| Overall stretch ratio [stretch ratio in MD * stretch ratio in CD] | 2.6:1 (1.61 * 1.61) |
| Basis weight of precursor web laminate [g/m$^2$] | 155 |
| Basis weight of stretched mechanical fastening web laminate [g/m$^2$] | 56 |
| MD tensile strength at break stretching of stretched mechanical fastening web laminate [N/25 mm] | 65.5 |

Examples 11-12

Example 11

Example 6 was repeated using FINATHENE 3868 at a polymer flow rate of 0.5 g/(hole*min) and a spinning speed of 3214 m/min. The filament titer obtained was 1.4 den. The basis weight of the spunbond fibrous web layer 11 was 50 g/m$^2$.

The fibrous web layer 11 obtained was then wound to a roll and for two weeks before it was fed into the nip to provide the precursor web laminate 10.

The sample was then simultaneously stretched in MD and CD after a conditioning period of 60 seconds in an oven at temperatures between 149° C. and 153° C. at a stretching speed of 10%/seconds in each direction with an adjusted stretch ratio of 2:1 in MD direction and 2:1 in CD direction.

The density of the male fastening elements 14 before and after stretching, the stretch ratios in MD and CD, the overall stretch ratio MD*CD, the basis weight of the precursor web laminate 10 and of the stretched mechanical fastening web laminate 1, and the MD-strength at break and the elongation at break of the stretched mechanical fastening web laminate 1 were measured as described above.

Example 12

Example 11 was repeated using blend 2 for forming the fibrous web layer 11. The fibrous web layer was stored for 2 weeks before laminating it to the thermoplastic web layer 13.

TABLE 5

Examples 11-12

| | Example | |
|---|---|---|
| | 11 | 12 |
| Density of male fastening elements before stretching [cm$^{-2}$] | 216 | 216 |
| Density of male fastening elements after stretching [cm$^{-2}$] | 63 | 76 |
| Overall stretch ratio [stretch ratio in MD * stretch ratio in CD] | 3.4:1 (1.84 * 1.84) | 2.8:1 (1.67 * 1.67) |
| Basis weight of precursor web laminate [g/m$^2$] | 182 | 179 |
| Basis weight of stretched mechanical fastening web laminate [g/m$^2$] | 52 | 61 |
| MD tensile strength at break of stretched mechanical fastening web laminate [N/25 mm] | 65.9 | 72.5 |

We claim:

1. A method of manufacturing a stretched mechanical fastening web laminate comprising a thermoplastic web layer having two major surfaces, one of the major surfaces bearing a multitude of male fastening elements suitable for engagement with a corresponding female fastening material, and on its other major surface a fibrous web layer, said method comprising the steps of (i) providing the fibrous web layer having an initial basis weight, wherein the fibrous web layer comprises one or more nonwoven materials free of staple fibers, (ii) passing the fibrous web layer through a nip formed by two rolls, one of them having cavities that are negatives of a plurality of male fastening elements; introducing a molten thermoplastic resin into the cavities in excess of an amount that would fill the cavities which excess forms the thermoplastic web layer, wherein a surface of the fibrous web layer is in continuous contact with the thermoplastic web layer; allowing the resin to at least partially solidify; and stripping of a precursor web laminate thus formed comprising the fibrous web layer and the thermoplastic web layer bearing the multitude of male fastening elements from the roll having cavities, wherein the thermoplastic web layer has an initial thickness and an initial density of male fastening elements, (iii) stretching the precursor web laminate monoaxially or biaxially thereby decreasing the basis weight of the fibrous web layer and the thickness of the thermoplastic web layer from their respective initial values to provide a stretched mechanical fastening laminate having a basis weight of less than 100 g/m$^2$, (iv) cutting through the stretched mechanical fastening web laminate in the cross-direction to form a portion of the stretched mechanical fastening web laminate, and (v) incorporating the portion into a component of a disposable absorbent article such that the male fastening elements are exposed and the fibrous web layer is not exposed.

2. The method according to claim 1, wherein the shape of the male fastening elements is modified prior to or after stretching by subjecting the male fastening elements to thermal, mechanical or radiation energy.

3. The method according to claim 1, wherein the fibrous nonwoven web layer comprises a plurality of filaments comprising at least one of natural fibers, spun yarn fibers, fibers of nylon, polyamides, polyesters or polyolefins, core-sheath bicomponent fibers, or monocomponent fibers.

4. The method according to claim 3, wherein the thermoplastic web layer of the precursor web laminate comprises a thermoplastic polymer comprising polyesters, polyamides or polyolefins.

5. The method according to claim 1, wherein the precursor web laminate is stretched sequentially or simultaneously biaxially in a cross-direction and a machine direction so that a stretch ratio of the resulting stretched mechanical fastening laminate relative to the precursor web laminate in the cross-direction and the machine direction is, independently from each other, between 1.1:1 and 10:1.

6. The method according to claim 5, wherein the product of the stretch ratio in the machine direction times the stretch ratio in the cross-direction is between 2:1 and 35:1.

7. The method according to claim 5, wherein the precursor web laminate is simultaneously biaxially stretched in a flat film tenter stretching apparatus.

8. The method according to claim 5, wherein the fibrous web layer comprised in the stretched mechanical fastening laminate has a basis weight of from 1 to 30 $g/m^2$.

9. The method according to claim 8, wherein a ratio of the initial basis weight of the fibrous web layer to the basis weight of the fibrous web layer comprised in the stretched mechanical fastening web laminate is between 3 and 40.

10. The method according to claim 8, wherein the stretched thermoplastic web layer has a thickness of between 5 and 25 μm.

11. The method according to claim 10, wherein a ratio of the initial thickness of the thermoplastic web layer of the precursor web laminate to the thickness of the thermoplastic web layer of the stretched mechanical fastening web laminate is between 3 and 40.

12. The method according to claim 1, wherein the density of the male fastening elements of the stretched mechanical fastening web laminate is between 2 and 200 per $cm^2$.

13. The method according to claim 1, wherein the stretched mechanical fastening web laminate exhibits a tensile strength in the machine direction as measured according to DIN EN ISO 527 of at least 15 N/25 mm.

14. The method according to claim 1, wherein the fibrous web layer has an initial basis weight of between 10 and 400 $g/m^2$.

15. The method according to claim 4, wherein precursor web laminate is stretched monoaxially in a machine-direction or a cross-direction so that a stretch ratio of the resulting stretched mechanical fastening laminate relative to the precursor web laminate is between 1.5:1 to 10:1.

16. The method according to claim 15, wherein monoaxially stretching is obtained by passing the precursor web laminate in the machine direction over rollers of increasing speed.

17. The method according to claim 1, wherein the stretched mechanical fastening web laminate exhibits a tensile strength at break that is higher than a tensile strength at break of a comparable thermoplastic web layer having a basis weight and a stretch ratio that are the same as the basis weight and stretch ratio of the stretched mechanical fastening web laminate.

18. The method according to claim 17, wherein the tensile strength at break of the stretched mechanical fastening web laminate is at least 10 percent higher than the tensile strength of the comparable thermoplastic web layer.

19. The method according to claim 1, wherein the fibrous web layer is a spunbond or melt blown nonwoven material.

20. The method according to claim 1, wherein the one or more nonwoven materials is point bonded or continuous bonded using at least one of heat or pressure.

21. A method of manufacturing a stretched mechanical fastening web laminate comprising a thermoplastic web layer having two major surfaces, one of the major surfaces bearing a multitude of male fastening elements suitable for engagement with a corresponding female fastening material, and on its other major surface a fibrous web layer, said method comprising the steps of (i) extruding the thermoplastic web layer bearing on one major surface a plurality of elongate spaced ribs in a machine direction with the cross-sectional shape of the ribs essentially corresponding to the cross-sectional shape of the male fastening elements to be formed, wherein the thermoplastic web layer has an initial thickness, (ii) providing the fibrous web layer having an initial basis weight, wherein the fibrous web layer comprises one or more nonwoven materials free of staple fibers, (iii) extrusion-laminating the fibrous web layer such that a surface of the fibrous web layer is in continuous contact with the major surface of the thermoplastic web layer opposite to the major surface bearing the elongate spaced ribs, thus providing a precursor web laminate, (iv) slitting the ribs in a cross-direction at spaced locations to form discrete portions of the ribs in the cross-direction with a length in the direction of the ribs essentially corresponding to a desired length of the male fastening elements to be formed, and stretching the precursor web laminate monoaxially or biaxially thereby decreasing the basis weight of the fibrous web layer and the thickness of the thermoplastic web layer from their respective initial values to provide a stretched mechanical fastening laminate having a basis weight of less than 100 $g/m^2$, (v) cutting through the stretched mechanical fastening web laminate in the cross-direction to form a portion of the stretched mechanical fastening web laminate, and (vi) incorporating the portion into a component of a disposable absorbent article such that the male fastening elements are exposed and the fibrous web layer is not exposed.

22. The method according to claim 21, wherein the stretched mechanical fastening web laminate exhibits a tensile strength at break that is higher than a tensile strength at break of a comparable thermoplastic web layer having a basis weight and a stretch ratio that are the same as the basis weight and stretch ratio of the stretched mechanical fastening web laminate.

23. The method according to claim 21, wherein the fibrous web layer is a spunbond or melt blown nonwoven material.

24. The method according to claim 21, wherein the one or more nonwoven materials is point bonded or continuous bonded using at least one of heat or pressure.

* * * * *